(12) United States Patent
Sullivan et al.

(10) Patent No.: US 11,918,324 B2
(45) Date of Patent: *Mar. 5, 2024

(54) ELECTRICAL COUPLING OF PULSE TRANSIT TIME (PTT) MEASUREMENT SYSTEM TO HEART FOR BLOOD PRESSURE MEASUREMENT

(71) Applicant: Apple Inc., Cupertino, CA (US)

(72) Inventors: Thomas J. Sullivan, Cupertino, CA (US); Wren Nancy Dougherty, San Francisco, CA (US); Richard C. Kimoto, Cupertino, CA (US); Erno Klaassen, Cupertino, CA (US); Ravi K. Narasimhan, Sunnyvale, CA (US); Stephen J. Waydo, Cupertino, CA (US); Todd K. Whitehurst, Cupertino, CA (US); Derek Park-Shing Young, Cupertino, CA (US); Santiago Quijano, Cupertino, CA (US); Zijing Zeng, Cupertino, CA (US)

(73) Assignee: Apple Inc., Cupertino, CA (US)

( * ) Notice: Subject to any disclaimer, the term of this patent is extended or adjusted under 35 U.S.C. 154(b) by 854 days.

This patent is subject to a terminal disclaimer.

(21) Appl. No.: 16/990,650

(22) Filed: Aug. 11, 2020

(65) Prior Publication Data

US 2020/0367767 A1 Nov. 26, 2020

Related U.S. Application Data

(63) Continuation of application No. 15/681,024, filed on Aug. 18, 2017, now Pat. No. 10,779,738, which is a
(Continued)

(51) Int. Cl.
*A61B 5/021* (2006.01)
*A61B 5/00* (2006.01)
(Continued)

(52) U.S. Cl.
CPC ...... *A61B 5/02125* (2013.01); *A61B 5/14551* (2013.01); *A61B 5/282* (2021.01);
(Continued)

(58) Field of Classification Search
CPC . A61B 5/02125; A61B 5/14551; A61B 5/282; A61B 5/681; A61B 5/6824; A61B 5/02416; A61B 5/053
See application file for complete search history.

(56) References Cited

U.S. PATENT DOCUMENTS 6,176,831 B1  1/2001  Voss et al.
6,228,034 B1  5/2001  Voss et al.
(Continued)

FOREIGN PATENT DOCUMENTS

EP   2191771     6/2010
WO   2014089665  6/2014
(Continued)

OTHER PUBLICATIONS

"National, State, and Local Area Vaccination Coverage Among Children Aged 19-35 Months—United States, 2011", Morbidity Mortality Weekly Report Weekly, vol. 61 No. 35, Sep. 7, 2012, 24 pages.
(Continued)

*Primary Examiner* — Eric F Winakur
*Assistant Examiner* — Abid A Mustansir
(74) *Attorney, Agent, or Firm* — Kilpatrick Townsend & Stockton LLP

(57) ABSTRACT

A pulse transit time is measured non-invasively and used to calculate a blood pressure value. A method of determining one or more blood pressure values includes propagating an alternating drive current through a thorax of a subject via electrodes located on a wrist-worn device. Resulting voltage levels of the subject are sensed by the wrist-worn device.
(Continued)

The voltage levels are processed to detect when a volume of blood is ejected from the left ventricle. Output from a pulse arrival sensor coupled to the wrist-worn device is processed to detect when a blood pressure pulse generated by ejection of the volume of blood from the left ventricle arrives at the wrist. A pulse transit time (PTT) for transit of the blood pressure pulse from the left ventricle to the wrist is calculated. One or more blood pressure values for the subject are determined based on the PTT.

20 Claims, 15 Drawing Sheets

Related U.S. Application Data continuation of application No. 15/507,401, filed as application No. PCT/US2015/048849 on Sep. 8, 2015, now abandoned.

(60) Provisional application No. 62/047,486, filed on Sep. 8, 2014.

(51) Int. Cl.
*A61B 5/024* (2006.01)
*A61B 5/053* (2021.01)
*A61B 5/1455* (2006.01)
*A61B 5/282* (2021.01)

(52) U.S. Cl.
CPC ............ *A61B 5/681* (2013.01); *A61B 5/6824* (2013.01); *A61B 5/02416* (2013.01); *A61B 5/053* (2013.01)

(56) References Cited

U.S. PATENT DOCUMENTS

| | | |
|---|---|---|
| 6,443,906 B1 | 9/2002 | Ting et al. |
| 6,514,211 B1 | 2/2003 | Baura |
| 6,554,774 B1 | 4/2003 | Miele |
| 6,676,600 B1 | 1/2004 | Conero et al. |
| 6,705,990 B1 | 3/2004 | Gallant et al. |
| 6,730,038 B2 | 5/2004 | Gallant et al. |
| 6,918,879 B2 | 7/2005 | Ting et al. |
| 6,932,772 B2 | 8/2005 | Kan |
| 6,974,419 B1 | 12/2005 | Voss et al. |
| 7,048,691 B2 | 5/2006 | Miele et al. |
| 7,144,372 B2 | 12/2006 | Ng et al. |
| 7,291,112 B2 | 11/2007 | Martin et al. |
| 7,317,409 B2 | 1/2008 | Conero |
| 7,318,807 B2 | 1/2008 | Ng |
| 7,361,147 B2 | 4/2008 | Ng |
| 7,503,896 B2 | 3/2009 | Miele et al. |
| 7,503,897 B2 | 3/2009 | Ng et al. |
| 7,867,170 B2 | 1/2011 | Gallant et al. |
| 7,871,381 B2 | 1/2011 | Ng et al. |
| 7,871,382 B2 | 1/2011 | Ng |
| 7,946,994 B2 | 5/2011 | Finburgh et al. |
| 7,976,471 B2 | 7/2011 | Martin et al. |
| 8,157,730 B2 | 4/2012 | Leboeuf et al. |
| 8,204,786 B2 | 6/2012 | Leboeuf et al. |
| D666,169 S | 8/2012 | Tucker et al. |
| 8,251,903 B2 | 8/2012 | Leboeuf et al. |
| 8,323,982 B2 | 12/2012 | LeBoeuf et al. |
| 8,328,727 B2 | 12/2012 | Miele et al. |
| 8,469,895 B2 | 6/2013 | Ting et al. |
| 8,506,497 B2 | 8/2013 | Katayama et al. |
| 8,512,242 B2 | 8/2013 | Leboeuf et al. |
| 8,597,195 B2 | 12/2013 | Gallant et al. |
| 8,647,270 B2 | 2/2014 | Leboeuf et al. |
| 8,652,040 B2 | 2/2014 | Leboeuf et al. |
| 8,652,409 B2 | 2/2014 | LeBoeuf et al. |
| 8,657,753 B2 | 2/2014 | Ting et al. |
| 8,672,854 B2 | 3/2014 | McCombie et al. |
| 8,700,111 B2 | 4/2014 | Leboeuf et al. |
| 8,702,607 B2 | 4/2014 | Leboeuf et al. |
| 8,777,862 B2 | 7/2014 | Finburgh et al. |
| 8,788,002 B2 | 7/2014 | LeBoeuf et al. |
| 2003/0167012 A1* | 9/2003 | Friedman ............ A61B 5/02125 600/506 |
| 2007/0038042 A1 | 2/2007 | Freeman et al. |
| 2008/0146890 A1 | 6/2008 | LeBoeuf et al. |
| 2008/0146892 A1 | 6/2008 | Leboeuf et al. |
| 2008/0220535 A1 | 9/2008 | LeBoeuf et al. |
| 2009/0112071 A1 | 4/2009 | LeBoeuf et al. |
| 2009/0216132 A1 | 8/2009 | Orbach et al. |
| 2011/0213254 A1 | 9/2011 | Ting |
| 2013/0059396 A1 | 3/2013 | LeBoeuf et al. |
| 2013/0131519 A1 | 5/2013 | LeBoeuf et al. |
| 2013/0172691 A1 | 7/2013 | Tran |
| 2013/0304112 A1 | 11/2013 | Ting et al. |
| 2013/0310677 A1* | 11/2013 | Chiu ................ A61B 5/02125 600/479 |
| 2014/0066732 A1 | 3/2014 | Addison et al. |
| 2014/0114147 A1 | 4/2014 | Romesburg |
| 2014/0128690 A1 | 5/2014 | LeBoeuf |
| 2014/0135596 A1 | 5/2014 | LeBoeuf et al. |
| 2014/0140567 A1 | 5/2014 | LeBoeuf et al. |
| 2014/0163399 A1 | 6/2014 | Gallant et al. |
| 2014/0171755 A1 | 6/2014 | LeBoeuf et al. |
| 2014/0171762 A1 | 6/2014 | LeBoeuf et al. |
| 2014/0180039 A1 | 6/2014 | LeBoeuf et al. |
| 2014/0275852 A1 | 9/2014 | Hong et al. |
| 2015/0112606 A1 | 4/2015 | He et al. |
| 2015/0119725 A1 | 4/2015 | Martin et al. |
| 2015/0164351 A1 | 6/2015 | He et al. |
| 2015/0265217 A1 | 9/2015 | Penders et al. |
| 2015/0366469 A1 | 12/2015 | Harris et al. |
| 2017/0042434 A1 | 2/2017 | Dias et al. |

FOREIGN PATENT DOCUMENTS

| | | |
|---|---|---|
| WO | 2015193551 | 12/2015 |
| WO | 2016040264 | 3/2016 |

OTHER PUBLICATIONS

"Non-invasive haemodynamic monitor", BioZ® Cardio Profile Device Manual, 2011, 42 pages.

"Prevention, Detection, Evaluation, and Treatment of High Blood Pressure", National High Blood Pressure Education Program, the Seventh Report of the Joint National Committee, 2004, 104 pages.

"Pulse Transit Time and Velocity Calculation", Biopac Systems, Inc., Mar. 21, 2006, 3 pages.

Allen, "Photoplethysmography and its application in clinical physiological measurement", Physiol. Meas. vol. 28, 2007, pp. R1-R39.

Ashraf et al., "Size of radial and ulnar artery in local population", J Pak Med Assoc, vol. 60, No. 10, Oct. 2010, pp. 817-819.

Baheti et al., "An ultra low power pulse oximeter sensor based on compressed sensing", Body Sensor Networks, IEEE, 2009, pp. 144-148.

Bang et al., "A Pulse Transit Time Measurement Method Based on Electrocardiogramand Bioimpedance", IEEE Biomedical Circuits and Systems Conference, 2009, pp. 153-156.

Cattivelli et al., "Noninvasive Cuffless Estimation of Blood Pressure from Pulse Arrival Time and Heart Rate with Adaptive Calibration", IEEE Computer Society, 2009, pp. 114-119.

Couceiro et al., "Characterization of Surrogate Parameters for Blood Pressure Regulation in Neurally-Mediated Syncope", 2013 35th Annual International Conference of the IEEE Engineering in Medicine and Biology Society (EMBC), 2013, pp. 5381-5385.

Critchley, "Minimally Invasive Cardiac Output Monitoring in the Year 2012", Artery Bypass, Mar. 13, 2013, pp. 45-80.

Cybulski et al., "Impedance Cardiography", Lecture Notes in Electrical Engineering, 2011, pp. 7-37.

Czajkowski et al., "Long-term Plan for Research and Translation in Hypertension for Enhancing Public Health", National Heart, Lung,

(56) References Cited

OTHER PUBLICATIONS and Blood Institute, National Institutes of Health Department of Health and Human Services, Dec. 2004, 77 pages.
Da Silva, "A pervasive system for real-time blood pressure Monitoring", Feb. 13, 2013, pp. 1-23.
Douniama, "Blood Pressure Estimation based on Pulse Transit Time and Compensation of Vertical Position", 3rd Russian-Bavarian Conference on Bio-Medical Engineering, 2007, 5 pages.
Douniama et al., "Blood Pressure Tracking Capabilities of Pulse Transit Times in Different Arterial Segments: A Clinical Evaluation", Computers in Cardiology, vol. 36, 2009, pp. 201-204.
Fagard, "Exercise characteristics and the blood pressure response to dynamic physical training", Med. Sci. Sports Exerc., vol. 33, No. 6,, 2001, pp. S484-S492.
Forouzanfar et al., "Coefficient-Free Blood Pressure Estimation Based on Pulse Transit Time-Cuff Pressure Dependence", IEEE Transactions on Biomedical Engineering, vol. 60, No. 7, Jul. 2013, pp. 1814-1824.
Gesche et al., "Continuous blood pressure measurement by using the pulse transit time: comparison to a cuff-based method", Eur J Appl Physiol, May 10, 2011, 7 pages.
Gesche et al., "Continuous blood pressure measurement by using the pulse transit time: comparison to a cuff-based method", Eur J Appl Physiol, vol. 112, 2012, pp. 309-315.
Harrison et al., "Portable acoustic myography—a realistic noninvasive method for assessment of muscle activity and coordination in human subjects in most home and sports settings", Physiological Reports ISSN 2051-817X, vol. 1, Iss.2, e00029, 2013, pp. 1-9.
Harwood-Smith et al., "Assessment of pulse transit time to indicate cardiovascular changes during obstetric spinal anaesthesia", British Journal of Anaesthesia, vol. 96 (1), 2006, pp. 100-105.
Hassan et al., "Non-invasive Continuous Blood Pressure Monitoring Based on PWTT", Journal of Advanced Computer Science and Technology Research, vol. 1, 2011, pp. 63-73.
He et al., "Evaluation of the Correlation Between Blood Pressure and Pulse Transit Time", IEEE, 2013, 4 pages.
Hennig et al., "Continuous blood pressure measurement using pulse transit time", Somnologie vol. 17, Jun. 6, 2013, pp. 104-110.
Hsiu et al., "Correlation of Harmonic Components between the Blood Pressure and Photoplethysmography Waveforms Following Local-Heating Stimulation", International Journal of Bioscience, Biochemistry and Bioinformatics, vol. 2, No. 4, Jul. 2012, pp. 248-253.
Hsiu et al., "Effects of Local-Heating Stimulation on the Harmonic Structure of the Blood Pressure and Photoplethysmography Waveforms", 2nd International Conference on Biomedical Engineering and Technology IPCBEE vol. 34, 2012, pp. 1-5.
Huotari et al., "Photoplethysmography and its detailed pulse waveform analysis for arterial stiffness", Rakenteiden Mekaniikka (Journal of Structural Mechanics), vol. 44, No. 4, 2011, pp. 345-362.
Jeong et al., "Continuous Blood Pressure Monitoring using Pulse Wave Transit Time", ICCAS, 2005, 4 pages.
Jobbagy, "Blood Pressure Measurement: Assessment of a Variable Quantity", 2010, pp. 316-324.
Kado et al., "RedTacton Near-body Electric-field Communications Technology and Its Applications", NTT Technical Review, vol. 8 No. 3, 2010, pp. 1-6.
Kalsi, "Design of Arterial Blood Pressure, Heart Rate Variability, and Breathing Rate Monitoring Device", Electrical and Biomedical Engineering Design Project (4BI6), Apr. 23, 2009, 65 pages.
Kim, "Design of Infrared Sensor Based Measurement System for Continuous Blood Pressure Monitoring Device", pp. 1-12.
Kim et al., "Development of an Arterial Tonometer Sensor", 31st Annual International Conference of the IEEE EMBS, Sep. 2-6, 2009, pp. 3771-3774.
Lima et al., "Use of Peripheral Perfusion Index Derived From the Pulse Oximetry Signal as a Noninvasive Indicator of Perfusion", Crit Care Med., vol. 30(6), 2002, 10 pages.
Marcinkevics et al., "Relationship between arterial pressure and pulse wave velocity using photoplethysmography during the post-exercise recovery period", Acta Universitatis Latviensis, vol. 753, Biology,, 2009, pp. 59-68.
Marinkovic, "Reconstructing the Blood Pressure Waveform using a Wearable Photoplethysmograph Sensor and Hydrostatic Pressure Variations Measured by Accelerometers", Submitted to the Department of Mechanical Engineering in Partial Fulfillment of the Requirements for the Degrees of Master of Science in Mechanical Engineering at the Massachusetts Institute of Technology, Feb. 2007, 54 pages.
Matthys et al., "Long-term pressure monitoring with arterial applanation tonometry: a non-invasive alternative during clinical intervention?", Technol Health Care, vol. 16, 2008, pp. 183-193.
McCarthy et al., "An examination of calibration intervals required for accurately tracking blood pressure using pulse transit time algorithms", Journal of Human Hypertension, 2013, pp. 1-7.
McCarthy, "An Investigation of Pulse Transit Time as a Non-Invasive Blood Pressure Measurement Method", Journal ofPhysics:ConferenceSeries. vol. 307, 2011, 6 pages.
McCombie et al., "Adaptive hydrostatic blood pressure calibration: Development of a wearable, autonomous pulse wave velocity blood pressure monitor", Proceedings of the 29th Annual International Conference of the IEEE EMBS, Aug. 23-26, 2007, pp. 370-373.
Meigas et al., "Continuous Blood Pressure Monitoring Using Pulse Wave Delay", 2001, 5 pages.
Nakamura et al., "Collaborative Processing of Wearable and Ambient Sensor System for Blood Pressure Monitoring", Sensors, 11, ISSN 1424-8220, www.mdpi.com/journal/sensors, 2011, pp. 6760-6770.
Norris et al., "Age Changes in Heart Rate and Blood Pressure Responses to Tilting and Standardized Exercise", Circulation, vol. VIII, Downloaded from http://circ.ahajournals.org/ at Cons California Dig Lib, Aug. 26, 2013, pp. 521-526.
O'Brien, "European Society of Hypertension International Protocol revision 2010 for the validation of blood pressure measuring devices in adults", Blood Pressure Monitoring, vol. 15, 2010, pp. 23-28.
O'Brien et al., "Working Group on Blood Pressure Monitoring of the European Society of Hypertension International Protocol for validation of blood pressure measuring devices in adults", Blood Pressure Monitoring, vol. 7, 2002, pp. 3-17.
O'Brien, "The British Hypertension Society protocol for the evaluation of automated and semiautomated blood pressure measuring devices with special reference to ambulatory systems", Journal of Ambulatory Monitoring, vol. 4, No. 3,, 1991, pp. 207-228.
Payne et al., "Pulse transit time measured from the ECG: an unreliable marker of beat-to-beat blood pressure", J Appl Physiol vol. 100, Sep. 1, 2005, pp. 136-141.
Proenca et al., "Is Pulse Transit Time a good indicator of Blood Pressure changes during short physical exercise in a young population?", 32nd Annual International Conference of the IEEE EMBS, Aug. 31-Sep. 4, 2020, pp. 598-601.
Raissuni et al., "Can We Obtain a Noninvasive and Continuous Estimation of Cardiac Output? Comparison Between Three Noninvasive Methods", Int Heart J, Nov. 2013, pp. 395-400.
Reisner et al., "Utility of the Photoplethysmogram in Circulatory Monitoring", Anesthesiology, vol. 108, 2008, pp. 950-958.
Sackl-Pietsch et al., "Continuous non-invasive arterial pressure shows high accuracy in comparison to invasive intra-arterial blood pressure measurement", 2014, pp. 1-5.
Seo, "Evaluation of cardiac output using nonuniform hybrid electrical impedance model based on forward lumped parameter and both-hands impedance measurement system", The Graduate School Yonsei University, Department of Biomedical Engineering, Feb. 2012, 146 pages.
Shaltis et al., "A Finite Element Analysis of Local Oscillometric Blood Pressure Measurements", Proceedings of the 29th Annual International Conference of the IEEE EMBS, Aug. 23-26, 2007, pp. 355-358.
Shaltis et al., "A hydrostatic pressure approach to cuffless blood pressure monitoring", Proceedings of the 26th Annual International Conference of the IEEE EMBS, Sep. 1-5, 2004, pp. 2173-2176.

(56) References Cited

OTHER PUBLICATIONS

Shaltis et al., "Calibration of the Photoplethysmogram to Arterial Blood Pressure: Capabilities and Limitations for Continuous Pressure Monitoring", Proceedings of the 2005 IEEE Engineering in Medicine and Biology 27th Annual Conference, Sep. 1-4, 2005, pp. 3970-3973.

Shaltis et al., "Cuffless Blood Pressure Monitoring Using Hydrostatic Pressure Changes", IEEE Transactions on Biomedical Engineering, vol. 55, No. 6,, Jun. 2008, pp. 1775-1777.

Shaltis et al., "Monitoring of Venous Oxygen Saturation Using a Novel Vibratory Oximetry Sensor", 2"d Joint Conference of the IEEE Engineering in Medicine and Biology, Society and the Biomedical Engineering Society, Oct. 23-26, 2002, pp. 1722-1723.

Shaltis et al., "Wearable, Cuff-less PPG-Based Blood Pressure Monitor with Novel Height Sensor", Proceedings of the 28th IEEE EMBS Annual International Conference, Aug. 30-Sep. 3, 2006, pp. 908-911.

Silverberg, "The unsupported arm: a cause of falsely raised blood pressure readings", British Medical Journal, Nov. 19, 1977, p. 1331.

Sinha et al., "Non-Invasive Blood Pressure Monitor: Beat to Beat", Technology Development Article, Barc Newsletter, Issue No. 328, Sep.-Oct. 2012, pp. 62-68.

Smith et al., "Pulse transit time: an appraisal of potential clinical applications", Thorax vol. 54, Available online at: http://thorax.bmj.com/content/54/5/452. full.html, Oct. 13, 2013, pp. 452-458.

Sola et al., "Continuous non-invasive blood pressure estimation", Diss. ETH. No. 20093, 2011, 196 pages.

Sola et al., "Noninvasive and Nonocclusive Blood Pressure Estimation via a Chest Sensor", IEEE Transactions on Biomedical Engineering, vol. 60, No. 12, Dec. 2013, pp. 3505-3513.

Sola et al., "Non-invasive monitoring of central blood pressure by electrical impedance tomography: first experimental evidence", Med Biol Eng Comput, vol. 49, 2011, pp. 409-415.

SomnoMedics, "Non-invasive, continuous and non-reactive blood pressure measurement using PTT", Medical Devices for Sleep Diagnostics and Therapy, 2012, pp. 1-20.

Song et al., "Estimation of Blood Pressure Using Photoplethysmography on the Wrist", Computers in Cardiology, vol. 36, 2009, pp. 741-744.

Sorvoja et al., "Noninvasive Blood Pressure Measurement Methods", Molecular and Quantum Acoustics, vol. 27, 2006, pp. 239-264.

Spulak et al., "Experiments With Blood Pressure Monitoring Using ECG and PPG", Czech Technical University in Prague, 5 pages.

Spulak et al., "Parameters for Mean Blood Pressure Estimation Based on Electrocardiogramand Photoplethysmography", Czech Technical University in Prague, 4 pages.

Teja, "Calculation of Blood Pulse Transit Time from PPG", Department of Biotechnology and Medical Engineering, National Institute of Technology, Rourkela 2012, 2012, 54 pages.

Theodor et al., "Implantable Acceleration Plethysmography for Blood Pressure Determination", 35th Annual International Conference of the IEEE EMBS, Jul. 3-7, 2013, pp. 4038-4041.

Thomas et al., "BioWatch—A wrist watch based signal acquisition system for physiological signals including blood pressure", 36th Annual International Conference of the IEEE Engineering in Medicine and Biology Society, Aug. 26, 2014, pp. 2286-2289.

Thompson et al., "Arteriosclerosis, Thrombosis, and Vascular Biology", Arterioscler Thromb Vase Biol. vol. 23, American Heart Association, Available online at: http://atvb.ahajournals.org/, 2003, pp. e42-e49.

Townsend, "Oscillometry", Medical Electronics, Michaelmas Term, 2001, pp. 48-54.

Van Dijk et al., "Oscillometry and applanation tonometry measurements in older individuals with elevated levels of arterial stiffness", Analytical methods and statistical analysis, Blood Pressure Monitoring vol. 18 No. 6, 2013, pp. 332-338.

Vignon-Clementel et al., "A Coupled Multidomain Method for Computational Modeling of Blood Flow", A Dissertation Submitted to the Department of Mechanical Engineering and the Committee on Graduate Studies of Stanford University in Partial Fulfillment of the Requirements for the Degree of Doctor of Philosophy, Jun. 2006, 207 pages.

Ward, "Blood Pressure Measurement", Cont Edu Anaesth Crit Care & Pain. vol. 7(4), 2007, pp. 122-126.

Wibmer et al., "Pulse transit time and blood pressure during cardiopulmonary exercise tests", Physiological Research Pre-Press Article, 2014, 26 pages.

Wikipedia, "Continuous noninvasive arterial pressure", Available online at: http://en.wikipedia.org/wiki/Continuous_noninvasive_arterial_pressure, Jul. 24, 2013, 8 pages.

Woidtke, "Pulse Transit Time and Peripheral Arterial Tonometry", 33 pages.

Wong et al., "An Evaluation of the Cuffless Blood Pressure Estimation Based on Pulse Transit Time Technique: a Half Year Study on Normotensive Subjects", Cardiovasc Eng. vol. 9, 2009, pp. 32-38.

Wong et al., "The Relationship between Pulse Transit Time and Systolic Blood Pressure on Individual Subjects after Exercises", Proceedings of the 1st Distributed Diagnosis and Home Healthcare (D2H2) Conference, Apr. 2-4, 2006, pp. 37-38.

Ye et al., "Estimation of Systolic and Diastolic Pressure using the Pulse Transit Time", World Academy of Science, Engineering and Technology 43, 2010, pp. 726-731.

Yong, "A computational system to optimise noise rejection in photoplethysmography signals during motion or poor perfusion states", Med Biol Eng Comput vol. 44, 2006, pp. 140-145.

Yoon et al., "Non-constrained Blood Pressure Monitoring Using ECG and PPG for Personal Healthcare", J Med Syst. vol. 33, 2009, pp. 261-266.

Zhang, "Cuff-Free Blood Pressure Estimation Using Signal Processing Techniques", Thesis for the degree of Master of Science in the Division of Biomedical Engineering University of Saskatchewan, http://hdl.handle.net/10388/etd-09082010-164956, Aug. 2010, 73 pages.

Zhang et al., "Pulse arrival time is not an adequate surrogate for pulse transit time as a marker of blood pressure", J Appl Physiol vol. 111, 2011, pp. 1681-1686.

* cited by examiner

ELECTRICAL COUPLING OF PULSE TRANSIT TIME (PTT) MEASUREMENT SYSTEM TO HEART FOR BLOOD PRESSURE MEASUREMENT

CROSS-REFERENCES TO RELATED APPLICATIONS

The present application is a Continuation of U.S. patent application Ser. No. 15/681,024 filed Aug. 18, 2017 (Allowed); which is a Continuation of U.S. patent application Ser. No. 15/507,401 filed Feb. 28, 2017; which is a U.S. National Stage Appln of PCT/US2015/048849 filed Sep. 8, 2015; which claims the benefit of U.S. Provisional Appln. No. 62/047,486 filed Sep. 8, 2014; the full disclosures of which are incorporated herein by reference in their entirety for all purposes.

BACKGROUND

Elevated blood pressure (a.k.a. hypertension) is a major risk factor for cardiovascular disease. As a result, blood pressure measurement is a routine task in many medical examinations. Timely detection of hypertension can help inhibit related cardiovascular damage via accomplishment of effective efforts in treating and/or controlling the subject's hypertension.

A person's blood pressure is a continuously changing vital parameter. As a result, sporadic office blood pressure measurements may be insufficient to detect some forms of hypertension. For example, hypertension can occur in a pattern that evades detection via isolated office blood pressure measurement. Common hypertension patterns include white coat hypertension (elevated only during a limited morning period of time), borderline hypertension (fluctuating above and below definitional levels over time), nocturnal hypertension (elevated only during sleeping hours), isolated systolic hypertension (elevated systolic pressure with non-elevated diastolic pressure), and isolated diastolic hypertension (elevated diastolic pressure with non-elevated systolic pressure). To detect such hypertension patterns, it may be necessary to perform additional blood pressure measurements over time to obtain a more complete view of a person's blood pressure characteristics. Although continuous measurement of blood pressure can be achieved by invasive means, for example, via an intra-arterial pressure sensing catheter, noninvasive blood pressure measurement approaches are more typically used.

Current noninvasive blood pressure measurement approaches include ambulatory and home blood pressure measurement strategies. These strategies provide such a more complete view of a person's blood pressure characteristics and are often employed in recommended situations. Ambulatory blood pressure measurement is performed while the person performs daily life activities. Currently, ambulatory blood pressure measurements are typically performed every 20 to 30 minutes using brachial oscillometric blood pressure measurement cuffs. Ambulatory blood pressure measurement may be recommended where the is large variability in office blood pressure measurements, where a high office blood pressure measurement is made in a person with otherwise low cardiovascular risk, when office and home blood pressure measurements vary, where resistance to drug treatment of blood pressure is noted or suspected, where hypotensive episodes are suspected, or where preclampsia is suspected in pregnant women. Home blood pressure measurement include isolated self-measurements performed by a person at home. Home blood pressure measurements may be recommended where information is desired regarding the effectiveness of blood pressure lowering medication over one or more dose-to-dose intervals and/or where doubt exists as to the reliability of ambulatory blood pressure measurement.

Current ambulatory and home blood pressure measurement approaches, however, fail to provide continuous measurement of blood pressure. Additionally, when an oscillometric blood pressure measurement cuff is used to monitor a person's blood pressure when sleeping, the intermittent inflation and deflation of the cuff can disturb the person's sleeping pattern, thereby harming the subject to some extent and potentially changing the person's sleeping blood pressure. Thus, convenient and effective approaches for noninvasive continuous measurement of blood pressure remain of interest.

BRIEF SUMMARY

Wrist-worn devices and related approaches are provided for continuous noninvasive measurement of blood pressure. In one approach, a wrist-worn device includes electrodes for detecting when blood is ejected from the user's left ventricle and a photo-plethysmogram (PPG) or a pulse pressure sensor for detecting when a blood pressure pulse corresponding to the ejected blood arrives at the user's wrist. The pulse transit time (PTT) for the blood pressure pulse from the ejection of the blood from the left ventricle to arrival of the blood pressure at the wrist is then used to calculate a blood pressure value for the user. In this approach, the blood pressure value is obtained in a noninvasive and non-occlusive approach without any additional device required.

Thus, in one aspect, a wrist-worn device is provided for determining a pressure of blood within a cardiovascular system of a user. The cardiovascular system includes a heart and the user has a wrist covered by skin. The wrist-worn device includes a first pair of electrodes that non-invasively engage the skin over the wrist of the user when the device is worn on the wrist, a second pair of electrodes that are externally located on the wrist-worn device, a photo-plethysmogram (PPG) or a pulse pressure sensor, and a controller. The first pair of electrodes includes a first drive current electrode and a first sense electrode. The first drive current electrode is configured to transfer a drive current between the first drive current electrode and the wrist. The first sense electrode is configured for sensing a first voltage level of the user. The second pair of electrodes is located so as to interfaceable with the user, for example, by touching with fingers on the user's arm opposite to the arm having the wrist on which the device is worn. The second pair of electrodes includes a second drive current electrode and a second sense electrode. The second drive current electrode is configured to transfer drive current between the second drive current electrode and the user. The second sense electrode is configured for sensing a second voltage level of the user. The photo-plethysmogram (PPG) or the pulse pressure sensor is coupled to the wrist-worn device for detecting the arrival of a blood pressure pulse at the user's wrist. The controller is configured to: 1) process a signal indicative of the sensed voltage levels to detect when blood is ejected from the left ventricle of the user's heart, 2) process a signal from the PPG or the pulse pressure sensor to detect when a blood pressure pulse corresponding to the ejected blood arrives at the user's wrist, 3) calculate a pulse transit time (PTT) for the blood pressure pulse from the ejection of the blood from the left ventricle to arrival of the blood pressure pulse at the wrist, and 4) generate one or more blood pressure values for the user based on the PTT.

The second pair of electrodes can be configured to be interfaced with a suitable region of the user's body so that a portion of the drive current travels through the thorax of the subject. For example, the second drive current electrode can be sized and positioned for contact by a first finger of an arm of the user opposite to the arm on which the device is worn. And the second sense current electrode can be sized and positioned to be contacted by a second finger of the opposite arm. As another example, the second pair of electrodes can be sized and positioned so as to be interfaceable with any suitable location on the opposite arm and/or with any other suitable location on the subject (e.g., a leg, abdomen, or thorax of the subject) so that a substantial portion of the drive current travels through the thorax of the subject.

The first and second pairs of electrodes can be positioned to enhance contact between the user's wrist and the first pair of electrodes. For example, each of the first drive current electrode and the first sense electrode can be disposed so that contact pressure between the first and second fingers and the second pair of electrodes increases contact pressure between the wrist and each of the first drive current electrode and the first sense electrode. The wrist-worn device can include a wrist-worn elongate band. The first and second pairs of electrodes can be disposed on the wrist band such that contact pressure on each of the second pair of electrodes causes: (a) increased contact pressure between the wrist band and a respective one of the first pair of electrodes, and (b) increased contact pressure with the respective one of the first pair of electrodes and the user's wrist.

The controller can be configured to generate an electrocardiogram (EKG) for the user from one or more signals from the first and second pair of electrodes. For example, the first and second sense electrodes can be used to detect voltage levels of the user used to generate the EKG.

Each of the first and second pair of electrodes can be a dry electrode. The use of dry electrodes avoids the use of disposable electrodes, such as silver/silver chloride gel-based electrodes.

The first and second sensing electrodes can be configured to detect a voltage difference resulting from the drive current. The voltage difference can be used to generate an impedance cardiogram (ICG) for the user.

In embodiments employing a PPG sensor, the PPG sensor can be configured to detect the arrive of the blood pressure pulse a greater depth into the wrist as compared to conventional PPG sensors. For example, the PPG sensor can include a light source and a plurality of light detectors. At least two of the light detectors can be disposed at different distances from the light source so to enable detection of different mean penetration depths of light emitted by the light source. The controller can be configured to process output from the light detectors to determine the amount of light returned from a deeper penetration depth relative to the detected mean penetration depths. At least two of the light detectors can be disposed in a range of 2 mm to 10 mm from the light source. The PPG sensor can include at least two light sources configured to emit different wavelengths of light so as to enable detection of a plurality of mean penetration depths for light emitted by the light sources. For example, the at least two light sources can include at least two of an infra-red light source, a red light source, or a green light source. The different wavelengths of light emitted can include a first wavelength of about 525 nm and a second wavelength of about 940 nm. The controller can be configured to process output from the detectors to determine the amount of light returned from a deeper penetration depth relative to the detected mean penetration depths. The PPG sensor can include both multiple light sources and multiple light detectors disposed at different distances from one or more of the light sources.

The greater detection depth can be used to monitor a deeper layer and/or a deeper artery within the wrist. For example, the controller can be configured to process signals from the light detectors to detect when the blood pressure pulse corresponding to the ejected blood arrives at the deep blood plexus (DBP) layer at the user's wrist. The PPG sensor can be positioned over a radial artery and configured to detect when the blood pressure pulse corresponding to the ejected blood arrives at the user's wrist within the user's radial artery. The controller can be configured to process signals from the light detectors to detect when the blood pressure pulse corresponding to the ejected blood arrives at the user's wrist within the user's radial artery.

The PPG sensor can be configured to detect levels of vasomotion (e.g., vasodilation, vasoconstriction) of the user's arteries. For example, the controller can be configured to process one or more signals from the light detectors to determine a tone of the user's blood vessels. The blood pressure value generated for the user can be further based on the determined tone of the user's blood vessels.

A pulse pressure sensor can be used instead of, or in combination with, the PPG sensor. In embodiments employing a pulse pressure sensor, the pulse pressure sensor is configured to detect the arrival of the blood pressure pulse at the user's wrist and includes at least one pressure transducer, accelerometer, or strain gauge positioned over a radial artery of the wrist of the user.

The controller can be further configured to calculate trending data for any suitable time period based on the one or more blood pressure values. For example, the time period can include one or more days, one or more weeks, one or more months, or one or more years.

The wrist-worn device can include any suitable combination of the features described herein. For example, the wrist-worn device can include any of the combinations of features recited in the claims included herein.

In another aspect, a method is provided for determining a pressure of blood within a cardiovascular system of a user. The cardiovascular system includes a heart and the user has a wrist covered by skin. The method includes propagating an alternating drive current through the subject between first and second drive current electrodes coupled to a wrist-worn device. The second drive current electrode is externally located on the device and engaged with the subject so that a portion of the alternating drive current travels through a thorax of the subject. The first drive current electrode non-invasively engages the skin on the wrist of the user. Voltage levels of the subject resulting from the drive current are sensed via first and second sense electrodes coupled to the wrist-worn device. The second sense electrode is externally located on the device and engaged with the subject so as to sense a voltage level induced by the drive current. The first sense electrode non-invasively engages the skin on the wrist of the user. The sensed voltage levels are processed to detect when blood is ejected from the left ventricle of the subject's heart. Output from a PPG or a pulse pressure sensor coupled to the wrist-worn device is processed to detect when a blood pressure pulse corresponding to the blood ejection arrives at the wrist. A pulse transit time (PTT) is calculated for the blood pressure pulse from the left ventricle to arrival of the blood pressure pulse at the wrist.

One or more relative blood pressure values are generated for the subject based on the PTT. The alternating drive current can be propagated and the voltage levels are sensed when the second drive current electrode and the second sense electrode are contacted by fingers of the opposite arm or with skin on the user's thorax.

The method can further include processing output from the PPG sensor to determine a tone of the subject's blood vessels. The one or more blood pressure values generated for the subject can be further based on the determined tone of the subject's blood vessels.

The generation of the one or more blood pressure values can be further based on calibration data including measured blood pressure values and corresponding PTTs for the subject. For example, an oscillometric blood pressure measurement cuff can be used to measure one or more blood pressure values for the subject at or at about the same time as when the method is used to calculate a corresponding one or more PTTs for the subject. Suitable calibration data can then be formulated using the oscillometric blood pressure measurement cuff measured blood pressure values and the corresponding one or more PTTs for the subject using known approaches. For example, a least squares method can be used to determine a suitable equation for blood pressure of the subject as a function of PTT. As another example, a suitable equation for blood pressure of the subject as a function of PTT can be predefined using any suitable approach, such as by entering coefficients of the equation or selecting a predefined equation based on one or more characteristics of the subject (e.g., age of the subject, whether the subject is male or female, and/or height to waist diameter of the subject).

The method can further include calculating trending data for a time period based on the one or more relative blood pressure values. Any suitable time period can be used, for example, one or more days, one or more weeks, one or more months, or one or more years.

The method can further include transmitting the one or more relative blood pressure measurements and/or the trending data to a suitable device. For example, the one or more blood pressure measurements and/or the trending data can be transmitted to a mobile device, table, computer, or database.

The method can further include generating an electrocardiogram (EKG) for the subject from one or more signals from the first and second pair of electrodes. The EKG can be used to detect when blood is ejected from the heart corresponding to the pressure pulse that arrives at the wrist.

The method can further include detecting different mean penetration depths of light emitted by the PPG sensor by at least one of: a) using at least two light detectors disposed at different distances from a light source of the PPG sensor; and b) using a plurality of light sources configured to emit different wavelengths of light. The method can include processing output from the light detectors to determine the amount of light returned from a deeper penetration depth relative to detected mean penetration depths.

The method can further include processing one or more signals from the PPG sensor to detect when the blood pressure pulse corresponding to the ejected blood arrives at a selected depth and/or location at the wrist. For example, the method can include processing one or more signals from the PPG sensor to detect when the blood pressure pulse corresponding to the ejected blood arrives at the deep blood plexus (DBP) layer at the subject's wrist. As another example, the method can include processing one or more signals from the PPG sensor to detect when the blood pressure pulse corresponding to the ejected blood arrives at the subject's wrist within the subject's radial artery.

The method can further include processing one or more signals from the PPG sensor to determine a tone of the subject's blood vessels. The one or more blood pressure values generated for the subject can be further based on the determined tone of the subject's blood vessels.

The method can include any suitable combination of the acts and/or features described herein. For example, the method can include any of the combinations of acts and/or features recited in the claims included herein.

In another aspect, a wrist-worn device is provided for determining a pressure of blood within a cardiovascular system of a user. The cardiovascular system includes a heart and the user has a wrist covered by skin. The device includes: 1) an elongate band extending around the wrist and non-invasively engaging the skin on the wrist of the user, 2) at least four EKG or ICG electrodes coupled to the elongate band for detecting a first signal indicative of ventricular ejection of the heart at an associated ventricular ejection time, 3) a photo-plethysmogram (PPG) sensor coupled to the elongate band for detecting a second signal indicative of arrival of a blood pressure pulse at the user's wrist corresponding to the first ventricular ejection signal and at an associated pulse arrival time, and 4) a controller configured to calculate a pulse transit time (PTT) for the blood pressure pulse from a difference between the ventricular ejection time and pulse arrival time and generate one or more relative blood pressure values for the user based on the PTT.

The PPG sensor can be configured to detect different mean penetration depths of light from the PPG sensor. For example, the PPG sensor can include a light source and a plurality of light detectors. At least two of the light detectors can be disposed at different distances from the light source so to enable detection of different mean penetration depths of light emitted by the light source. As another example, the PPG sensor can include at least two light sources configured to emit different wavelengths of light so as to enable detection of a plurality of mean penetration depths for light emitted by the light sources.

In another aspect, a device is provided for determining a pressure of blood within a cardiovascular system of a user having a wrist and a radial artery. Skin forms an outer surface of the wrist. The wrist-worn device includes a first photo-plethysmogram (PPG) or a first pulse pressure sensor coupled to the wrist-worn device, a second photo-plethysmogram (PPG) or a second pulse pressure sensor mountable to the user at a mounting location offset from the user's wrist, and a controller. The first PPG or the first pulse pressure sensor non-invasively engages the skin of the user over a wrist and is positioned over the radial artery of the wrist of the user so as to detect the arrival of a blood pressure pulse at the user's wrist. The second PPG or the second pulse pressure sensor is configured for detecting the arrival of the blood pressure pulse at the mounting location of the second PPG sensor. The controller is configured to: 1) process a signal from the first PPG or pressure sensor to detect when the blood pressure pulse arrives at the user's wrist, 2) process a signal from the second PPG or the second pulse pressure sensor to detect when the blood pressure pulse arrives at the mounting location of the second PPG sensor, 3) calculate a pulse transit time (PTT) for the blood pressure pulse between the mounting location of the second PPG sensor and the user's wrist, and 4) generate one or more blood pressure values for the user based on the PTT. In many embodiments, the mounting location is an arm or finger of the user.

The preceding presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

For a fuller understanding of the nature and advantages of the present invention, reference should be made to the ensuing detailed description and accompanying drawings.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Figure 1:
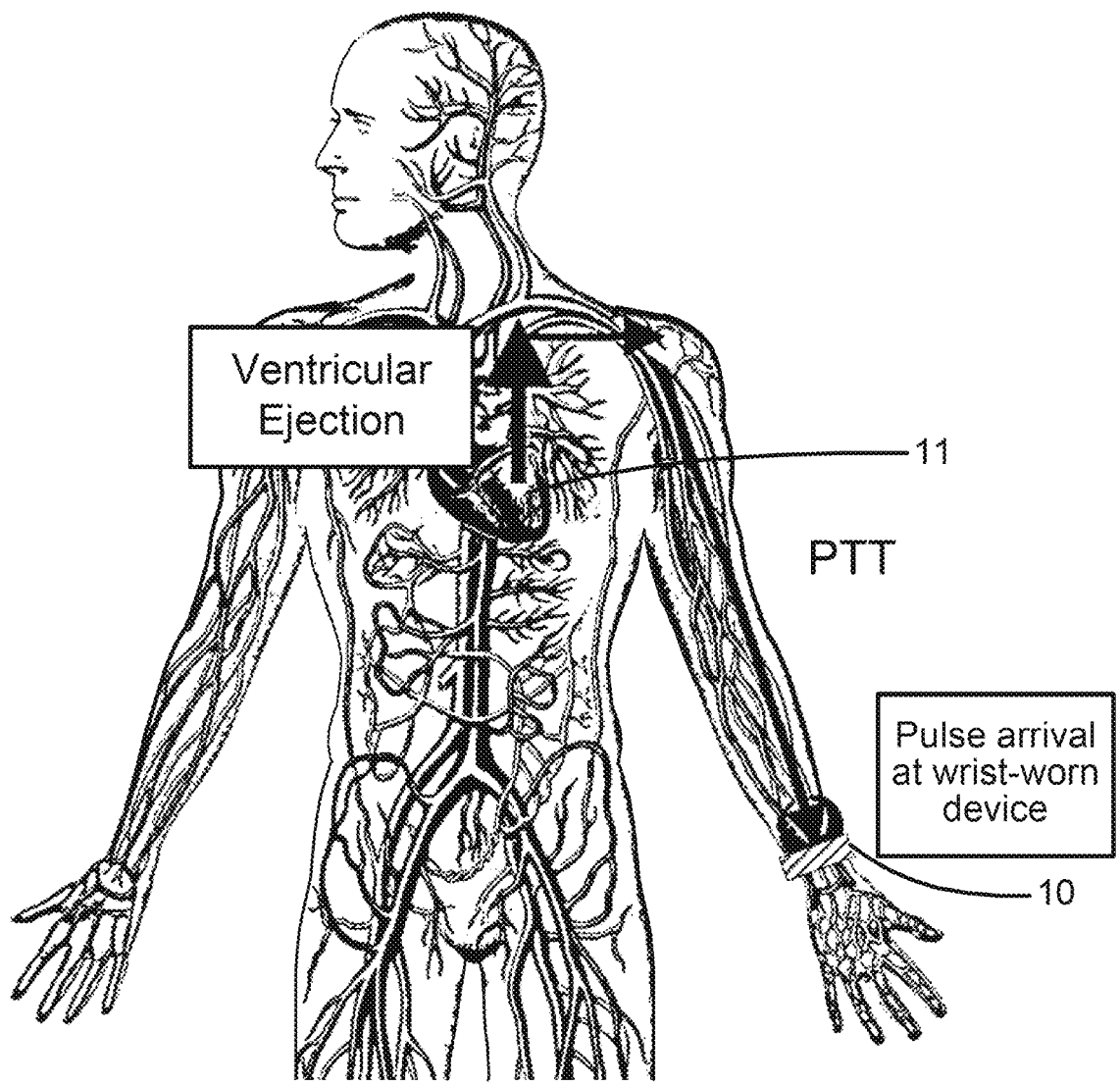
FIG. 1 illustrates a propagation path of a blood pressure pulse from ejection from the left ventricle to a wrist on which a wrist-worn blood pressure measurement device is worn, in accordance with many embodiments.

Referring now to the drawings, in which like reference numerals represent like parts throughout the several views, FIG. 1 illustrates a propagation path of a blood pressure pulse from ejection from the left ventricle of a subject's heart to a wrist on which a wrist-worn blood-pressure measurement device 10 is worn, in accordance with many embodiments. The wrist-worn device 10 is configured to detect when the blood corresponding to the blood pressure pulse is ejected from the left ventricle of a subjects heart and when the blood pressure pulse arrives at the wrist-worn device 10. The wrist-worn device 10 is configured to calculate a pulse transit time (PTT) for the blood pressure pulse for the transit of the blood pressure pulse from the left ventricle to the wrist-worn device 10. The determined PTT is then used to determine one or more blood-pressure values for the subject.

In general, a PTT is the time it takes for a pulse pressure wave to propagate through a length of a subject's arterial tree. PTT has a nonlinear relationship with blood pressure. Factors that can impact how fast a blood pressure pulse will travel at a given blood-pressure in a particular artery, include, for example, arterial stiffness, arterial wall thickness, and arterial inner diameter. Equation (1) provides a functional relationship between PTT and mean arterial blood pressure (MAP).

$$MAP = \frac{1}{\alpha} \ln\left[\frac{\rho D (\Delta d)^2}{h E_0 (PTT)^2}\right] \quad (1)$$

where: MAP is mean arterial blood pressure;
PTT is Pulse Transit Time;
h is arterial wall thickness;
D is artery diameter;
$\rho$ is density of blood;
$E_0$ is the Young's modulus of the artery at zero pressure;
$\alpha$ is a subject dependent physiological constant; and
$\Delta d$ is the arterial distance between the subjects left ventricle and the wrist.

The pressure pulse travels through different arteries during its transit from the left ventricle to the wrist. As a result, variation in corresponding variables in equation (1), for example, arterial wall thickness (h), artery diameter (D), and Young's modulus of the artery at zero pressure ($E_0$), will change the relationship between blood pressure and how fast the blood pressure pulse travels through the respective artery. Each blood pressure pulse, however, will travel through the same arteries during transit from the left ventricle to the wrist. Accordingly, a relationship between the overall PTT from the left ventricle to the wrist and MAP can be given by replacing arterial wall thickness (h), artery diameter (D), and Young's modulus of the artery at zero pressure ($E_0$) with respective effective values suitable for the combination of all the arteries through which the pressure pulse travels from the left ventricle to the wrist. Therefore, equation (1) can be simplified to the relationship given below in equation (2).

$$MAP = \frac{1}{\alpha} \ln\left[\frac{K}{(PTT)^2}\right] \quad (2)$$

where:

$$K = \frac{\rho D(\Delta d)^2}{hE_0}$$

is suitable for the subject and the arterial tree segment over which PTT is being measured.

The values of (K) and (α) can be determined using any suitable approach. For example, an oscillometric blood pressure measurement cuff can be used to measure one or more blood pressure values for the subject at or at about the same time as when corresponding one or more PTTs are determined for the subject via the wrist-worn device 10. Suitable calibration data can then be formulated using the oscillometric blood pressure measurement cuff measured blood pressure values and the corresponding one or more PTTs for the subject using known approaches. For example, a least squares method can be used to determine suitable values or relationships for determining the values of (K) and (α).

A similar approach can be used to predict MAP, systolic blood pressure (SBP), and diastolic blood pressure (DBP) values based on a measured PTT value. For example, equations (3), (4), and (5) are example regression equations that can be used to predict MAP, SBP, and DBP, respectively, from a measured PTT.

$$MAP = K_{MAP} \times [\log(PTT) - \log(PTT_0)] + MAP_{BASELINE} \quad (3)$$

where: MAP is predicted mean arterial blood pressure;
$MAP_{BASELINE}$ is a baseline measured MAP;
$K_{MAP}$ is a subject dependent constant for MAP;
PTT is the measured pulse transit time; and
$PTT_0$ is the measured pulse transit time for $MAP_{BASELINE}$.

$$SBP = K_{SBP} \times [\log(PTT) - \log(PTT_0)] + SBP_{BASELINE} \quad (4)$$

where: SBP is predicted systolic blood pressure;
$SBP_{BASELINE}$ is a baseline measured systolic blood pressure;
$K_{SBP}$ is a subject dependent constant for systolic blood pressure;
PTT is the measured pulse transit time; and
$PTT_0$ is the measured pulse transit time for $SBP_{BASELINE}$.

$$DBP = K_{DBP} \times [\log(PTT) - \log(PTT_0)] + DBP_{BASELINE} \quad (5)$$

where: DBP is predicted diastolic blood pressure;
$DBP_{BASELINE}$ is a baseline measured diastolic blood pressure;
$K_{DBP}$ is a subject dependent constant for diastolic blood pressure;
PTT is the measured pulse transit time; and
$PTT_0$ is the measured pulse transit time for $DBP_{BASELINE}$.

Figure 2:
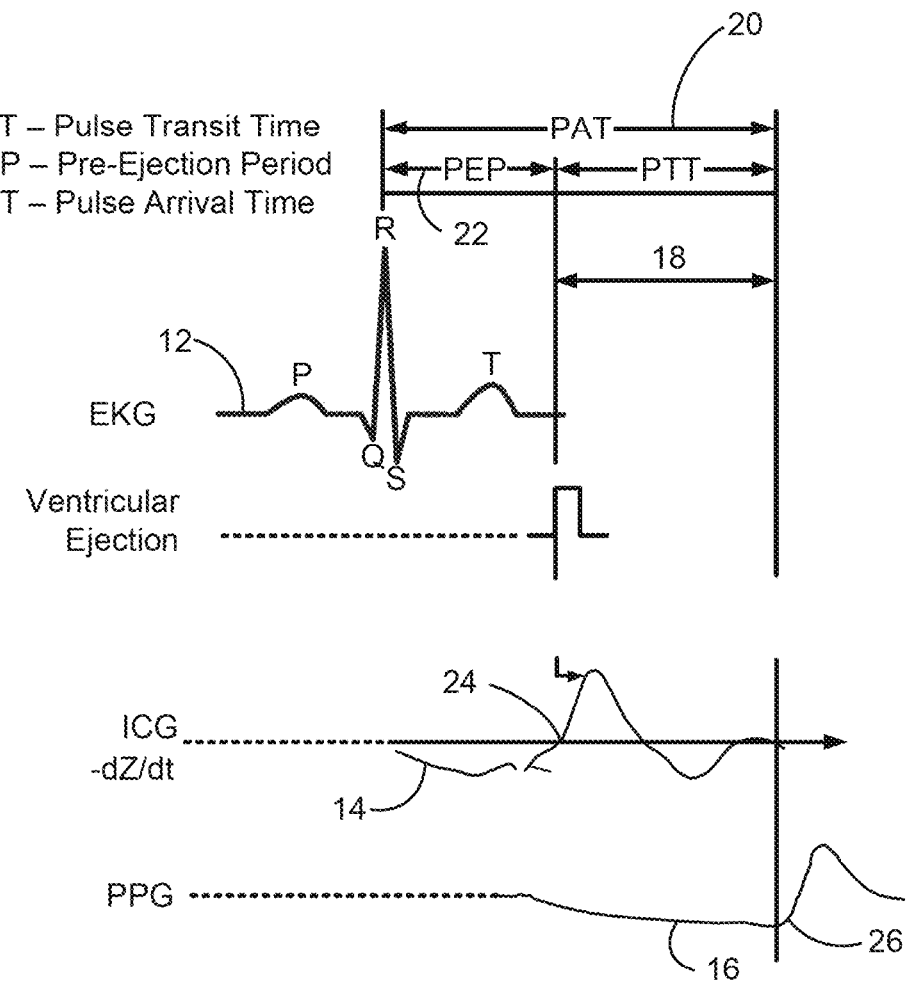
FIG. 2 illustrates EKG, ICG, and PPG signals relative to a pulse transit time (PTT) for a blood pressure pulse propagating from the left ventricle to a wrist on which a wrist-worn blood pressure measurement device is worn, in accordance with many embodiments.

FIG. 2 shows an EKG trace segment 12, an ICG trace segment 14, and a PPG signal 16 relative to a pulse transit time (PTT) 18 for a blood pressure pulse between the left ventricle of the subject to the wrist-worn device 10. In many embodiments, the wrist-worn device 10 includes electrodes used to generate an EKG trace and an ICG trace for the subject and a PPG sensor to generate a PPG signal for the subject. The EKG trace segment 12 has a segment (QRS) known as the QRS complex, which reflects the rapid depolarization of the right and left ventricles. The prominent peak (R) of the EKG trace corresponds to beginning of contraction of the left ventricle. A pulse arrival time (PAT) 20 is the time between the peak (R) of the EKG trace and arrival of the blood pressure pulse at the wrist-worn device 10. As the left ventricle contacts, pressure builds within the left ventricle to a point where the pressure exceeds pressure in the aorta thereby causing the aortic valve to open. A pre-ejection period (PEP) 22 is the time period between the peak (R) of the EKG trace and the opening of the aortic valve. The PEP 22 correlates poorly with blood pressure. The ICG trace 14 provides a better indication as to when the aortic valve opens. The ejection of blood from the left-ventricle into the aorta results in a significant temporary decrease in the thoracic impedance of the subject, which corresponds to a temporary increase in the ICG trace, which is the negative of the change of impedance with time. Accordingly, in many embodiments, the ICG trace 14 is processes to identify a start 24 of the temporary increase in the ICG trace as corresponding to the opening of the aortic valve and the start of the propagation of the blood pressure pulse. In many embodiments, the arrival of the blood pressure pulse is detected via the PPG signal 16, which includes an inflection point 26 that occurs upon arrival of the blood pressure pulse to the wrist-worn device 10.

Figure 3:
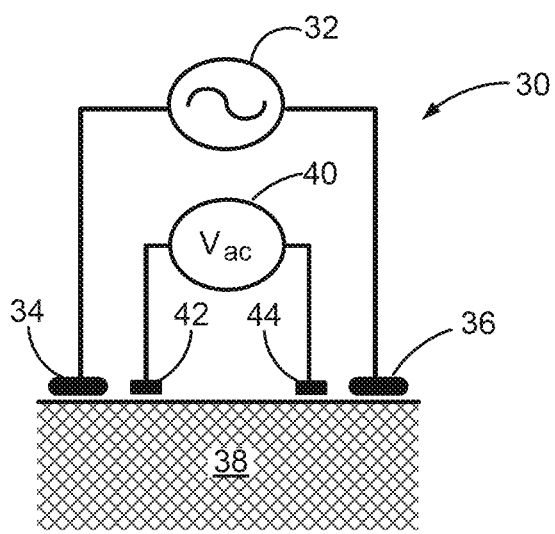
FIG. 3 schematically illustrates a four-electrode configuration used to measure impedance of a subject, in accordance with many embodiments.

FIG. 3 schematically illustrates a four-electrode configuration 30 used to measure impedance of a subject, in accordance with many embodiments. The four-electrode configuration 30 includes a drive current generator 32 electrically coupled with a first drive current electrode 34 and a second drive current electrode 36. In many embodiments, the drive current generator 32 imparts an alternating current to a subject 38 via the electrodes 34, 36. The four-electrode configuration 30 also includes a voltage sensor 40 electrically coupled with a first sense electrode 42 and a second sense electrode 44. The use of the sense electrodes 42, 44, which are separated from the drive current electrodes 34, 36, serves to reduce the impact of impedance and contract resistance by sensing voltage with electrodes that are transferring much lower levels of current relative to the current drive electrodes 34, 36. In many embodiments, the alternating drive current has a frequency between 20 kHz and 100 kHz. Drive currents below 20 kHz may create muscle excitation. And while drive currents at 100 kHz produces skin-electrode impedance approximately 100 times lower than at low frequencies, applied drive currents at greater than 100 kHz may result in stray capacitance. A drive current of about 85 kHz is preferred.

Figure 4:
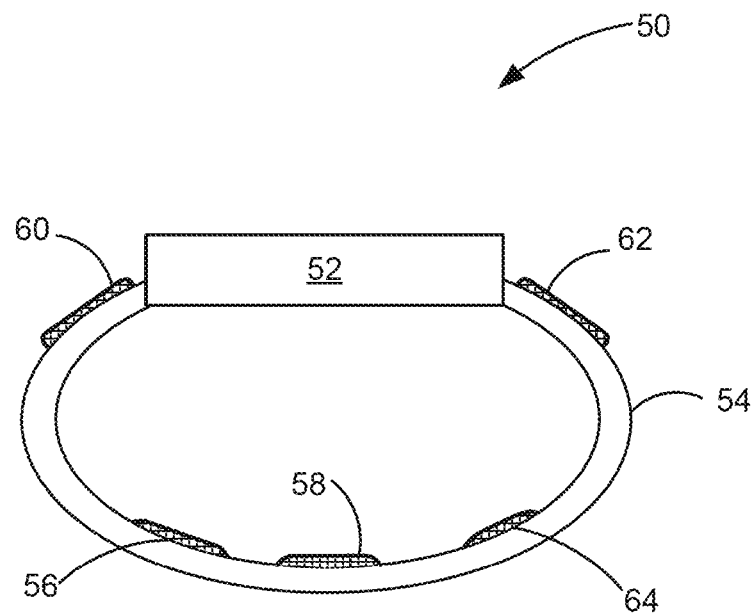
FIG. 4 is a schematic side view of a wrist-worn blood-pressure measurement device, in accordance with many embodiments.

FIG. 4 shows a side view of a wrist-worn blood-pressure measurement device 50, in accordance with many embodiments. The wrist-worn device 50 includes a main unit 52, a wrist-worn elongate band 54, a first drive current electrode 56, a first sense electrode 58, a second drive current electrode 60, a second sense electrode 62, and a PPG sensor 64.

The first drive current electrode 56, the first sense electrode 58, and the PPG sensor 64 are: 1) supported on the wrist-worn elongate band 54, 2) positioned and oriented to interface with a subject's wrist upon which the wrist-worn device 50 is worn, and 3) operatively connected with the main unit 52. The second drive current electrode 60 and the second sense electrode 62 are: 1) supported on the wrist-worn elongate band, 2) positioned and oriented to be interfaceable with the subject so that the drive current travels through the thoracic cavity of the subject (e.g., with separate fingers on the arm opposite to the arm on which the wrist-worn device 50 is worn), and 3) operatively connected with the main unit 52. The main unit 52 includes circuitry and/or software for imparting drive current through the subject via the first and second drive current electrodes 56, 60 and for processing signals from the PPG sensor 64 and the first and second sense electrodes 58, 62 so as to measure a PTT and calculate one or more blood pressure values for the subject based on the PTT.

Figure 5:
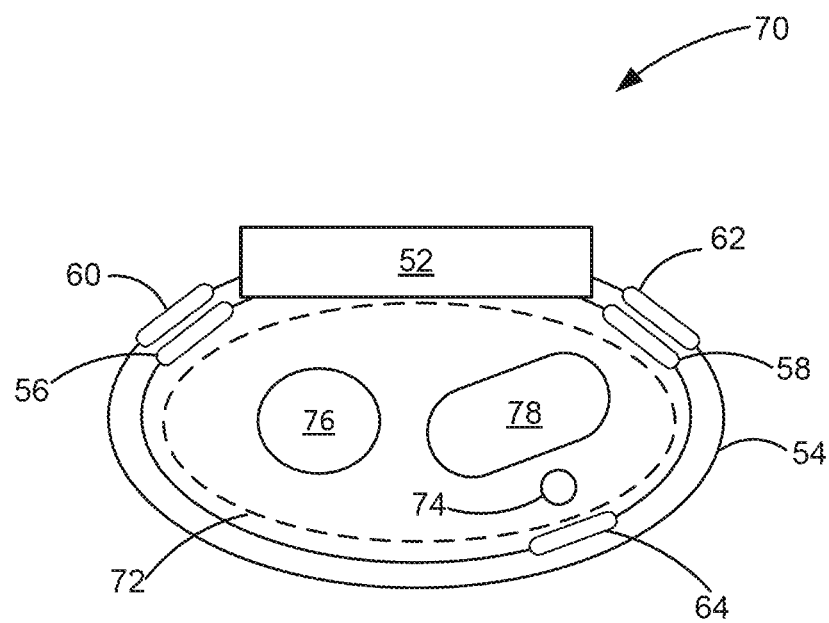
FIG. 5 is a cross-sectional view of another wrist-worn blood-pressure measurement device, in accordance with many embodiments.

FIG. 5 shows a side view of another wrist-worn blood-pressure measurement device 70, in accordance with many embodiments. The wrist-worn device 70 includes the same components as for the wrist-worn device 50, but has the first drive current electrode 56 and the first sense electrode 58 located to enhance contact pressure with a wrist 72 of the subject. In the illustrated embodiment, the first drive current electrode 56 is disposed on a directly opposite inside surface of the wrist-worn band 54 relative to the second drive current electrode 60 such that contact pressure between, for example, a finger of the subject and the second drive current electrode 60 transfers compression through the wrist-worn band 54 to the first drive current electrode 56, thereby increasing contact pressure between the first drive current electrode 56 and the wrist 72. In a similar fashion, the first sense electrode 58 is disposed on a directly opposite inside surface of the wrist-worn band 54 relative to the second sense electrode 62 such that contact pressure between, for example, a finger of the subject and the second sense electrode 62 transfers compression through the wrist-worn band 54 to the first sense electrode 58, thereby increasing contact pressure between the first sense electrode 58 and the wrist 72. Any suitable variation can be used. For example, the locations of the first drive current electrode 56 and the first sense electrode 58 can be exchanged. As another example, the electrodes 56, 58, 60, 62 can be located at any other suitable locations on the wrist-worn band 54. As another example, any suitable number of the electrodes 56, 58, 60, 62 can be disposed on the main unit 52.

In the illustrated embodiment, the PPG sensor 64 is located on the wrist-worn band 54 so as to be disposed to sense the arrival of the blood-pressure pulse within a radial artery 74 of the subject. Cross sections of the ulna bone 76 and the radius bone 78 of the subject are shown for reference.

Figure 6:
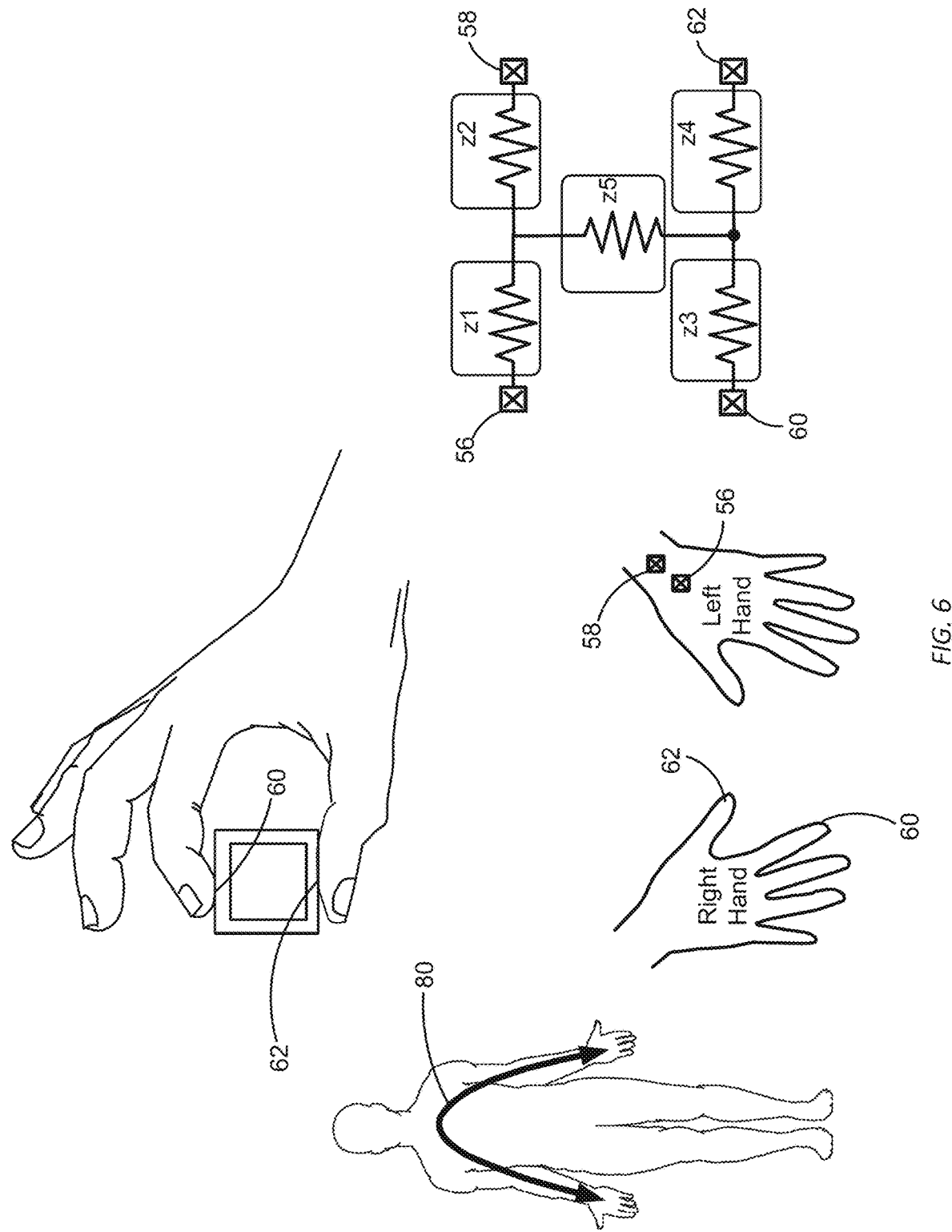
FIG. 6 schematically illustrates electrode locations and related body impedances in an approach for measuring chest-cavity impedance variations, in accordance with many embodiments.

FIG. 6 schematically illustrates electrode locations and related body impedances in an approach for measuring chest cavity impedances, in accordance with many embodiments. In the illustrated approach, the first drive current electrode 56 and the first sense electrode 58 are held in contact with the left wrist of the subject. The second drive current electrode 60 is contacted by the right index finger of the subject. The second sense electrode 62 is contacted by the right thumb of the subject. The first and second drive current electrodes 56, 60 impart a cross-body alternating drive current 80 between the drive current electrodes 56, 60. The cross-body drive current 80 propagates through the left wrist, through the left arm, through the thoracic cavity, through the right arm, and through the right index finger. The combined impedance of the left wrist local to the first drive current electrode 56 and the contact impedance of the first drive current electrode 56 and the left wrist is schematically represented as an impedance (Z1). The combined impedance of the right index finger in contact with the second drive current electrode 60 and the contact impedance of the second drive current electrode 60 and the right index finger is schematically represented as an impedance (Z3). The net cross-body impedance between the impedances (Z1 and Z3) is schematically represented as an impedance (Z5). The combined impedance of the left wrist local to the first sense electrode 58 and the contact impedance of the first sense electrode 58 and the left wrist is schematically represented as an impedance (Z2). The combined impedance of the right thumb in contact with the second sense electrode 62 and the contact impedance of the second sense electrode 62 and the right thumb is schematically represented as an impedance (Z4). In many embodiments, because the first and second sense electrodes 58, 62 are configured to measure a voltage difference without transferring any significant amount of current, the resulting voltage drops across the impedances (Z2 and Z4) are small so that the voltage difference sensed by the first and second sense electrodes 58, 62 matches the voltage difference across the impedance (Z5).

Figure 6A:
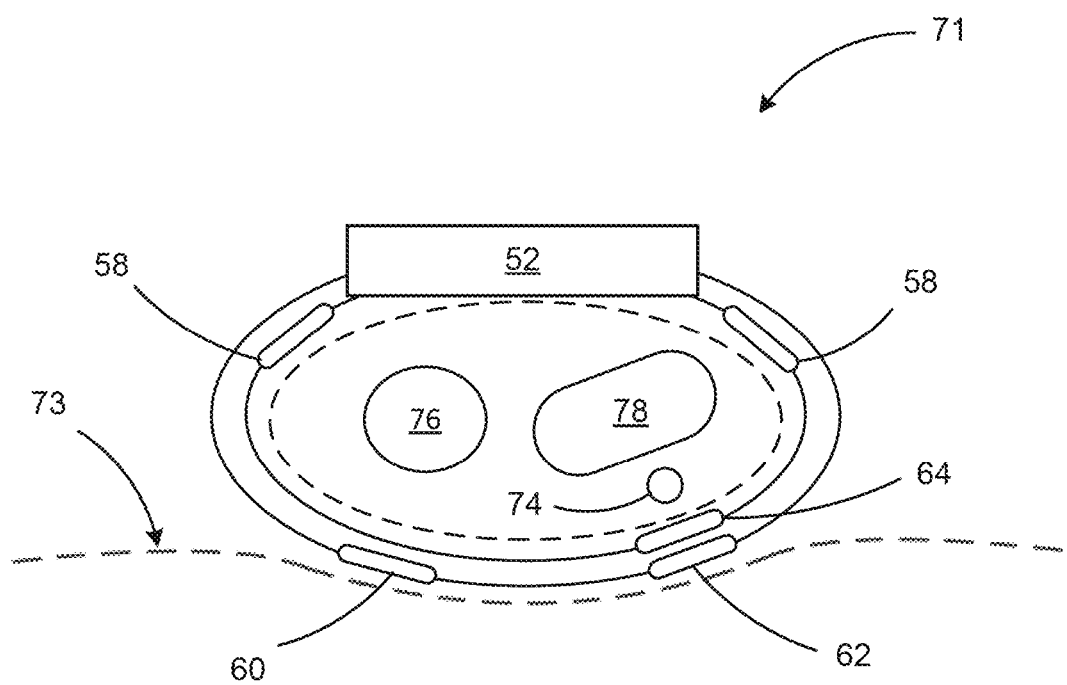
FIG. 6A is a cross-sectional view of another wrist-worn blood-pressure measurement device having exterior electrodes shown engaged with skin of a user's thorax, in accordance with many embodiments.

FIG. 6A shows a side view of another wrist-worn blood-pressure measurement device 71, in accordance with many embodiments. The wrist-worn device 71 includes the same components as for the wrist-worn device 70, but has the second drive current electrode 60 and the second sense electrode 62 located so that they can be engaged with another portion of the user via the user positioning the arm on which the wrist-worn device 71 is worn so as to press the electrodes 60, 62 into contact with any suitable skin portion of the user. For example, FIG. 6A illustrates the electrodes 60, 62 being pressed against a skin location on the user's thorax 73 (e.g., lower breast skin opposite to the arm on which the device 71 is worn). As another example, the electrodes 60, 62 can be pressed against skin on the user's arm opposite to the arm on which the device 71 is worn.

Figure 7:
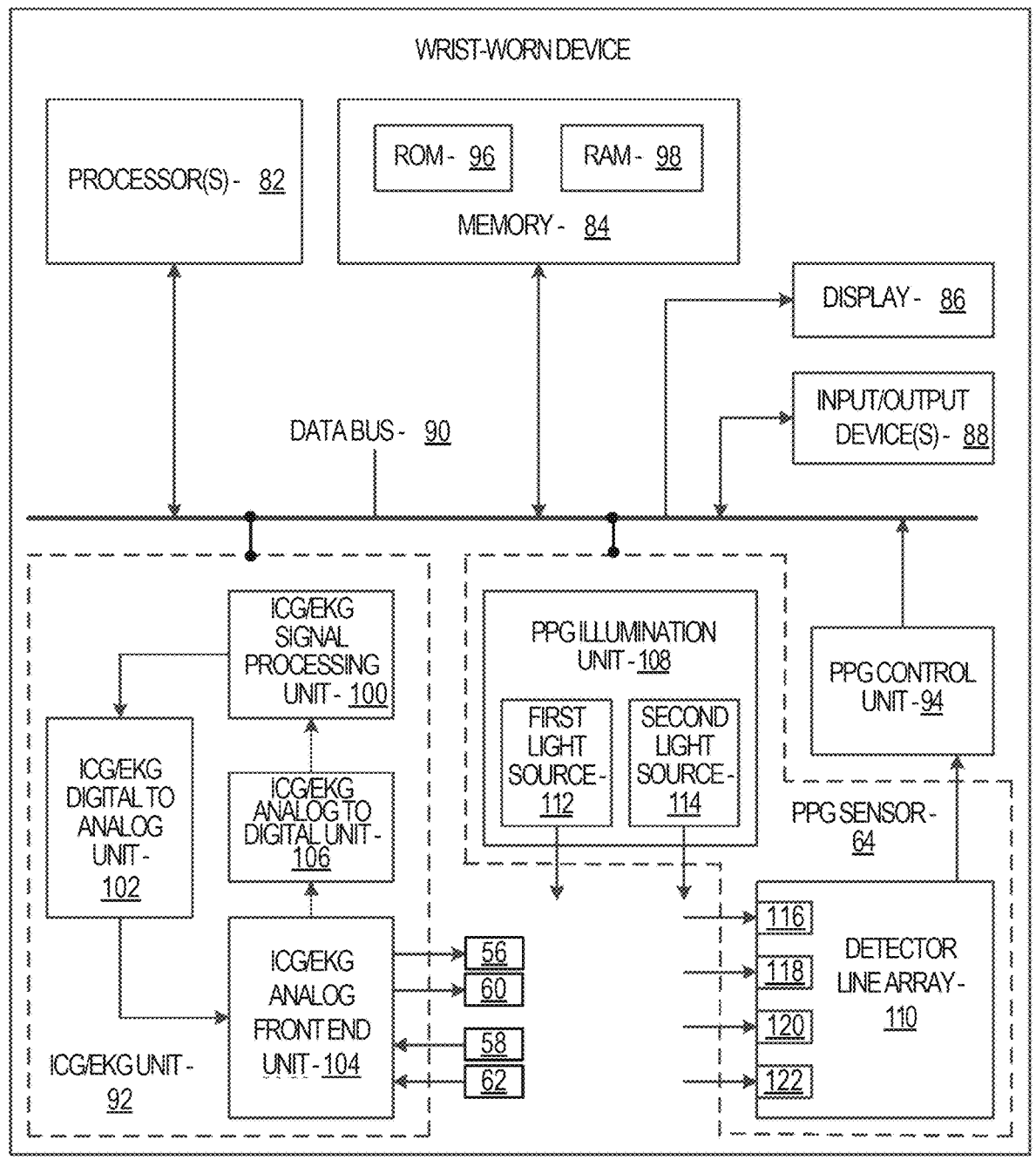
FIG. 7 is a schematic diagram of a wrist-worn blood-pressure measurement device main unit, in accordance with many embodiments.

FIG. 7 schematically represents an embodiment of a wrist-worn device for measuring blood pressure. In the illustrated embodiment, the wrist-worn device includes one or more processors 82, memory 84, a display 86, one or more input/output devices 88, a data bus 90, an ICG/EKG unit 92, the PPG sensor 64, and a PPG sensor control unit 94. In many embodiments, the memory 84 includes read only memory (ROM) 96, and random access memory (RAM) 98. The one or more processors 82 can be implemented in any suitable form, including one or more field-programmable gate arrays (FPGA).

The ICG/EKG unit 92 includes an ICG/EKG signal processing unit 100, an ICG/EKG digital to analog unit 102, an ICG/EKG analog front end unit 104, and an ICG/EKG analog to digital unit 106. The signal processing unit 100 generates a digital alternating drive signal (e.g., a digital drive signal corresponding to an 85 kHz sinusoidal drive current) and supplies the digital alternating drive signal to the digital to analog unit 102. The digital to analog unit 102 generates a sinusoidal drive current matching the digital alternating drive signal and supplies the sinusoidal drive current to the analog front end unit 104. The analog front end unit 104 supplies the sinusoidal drive current to the first and second drive current electrodes 56, 60 for propagation through the subject (e.g., as the cross-body alternating drive current 80 illustrated in FIG. 6). Resulting voltage levels are sensed via the first and second sense electrodes 58, 62.

Signals from the sense electrodes 58, 62 are processed by the analog front end unit 104 to generate an analog voltage signal supplied to the analog to digital unit 106. The analog to digital unit 106 converts analog voltage signal to a corresponding digital signal that is supplied to the signal processing unit 100. The signal processing unit 100 then generates corresponding ICG/EKG digital data that can be processed by the one or more processors 82 to determine the opening of the aortic valve and therefore the corresponding start of the propagation of a blood pressure pulse from the left ventricle to the wrist-worn device.

The PPG sensor unit 64 includes a PPG illumination unit 108 and detector line array 110. The PPG illumination unit 108 includes two light sources 112, 114 which transmit light having different wavelengths onto the wrist. While any suitable wavelengths can be used, the first light source 112 generates a beam of light having a wavelength of 525 nm. The second light source 114 generates a beam of light having a wavelength of 940 nm. Any suitable number of light sources and corresponding wavelengths can be used and selected to provide desired variation in tissue penetrating characteristics of the light. The detector line array 110 can include any suitable number of light detectors. In many embodiments, the light detectors are disposed at a plurality of different distances from the light sources 112, 114 so that the detected light is associated with different mean penetration depths so as to enable detection of the arrival of the blood pressure pulse at different layers and/or within a layer of the wrist deeper than a layer sensed by a single light source and single detector PPG sensor. In the illustrated embodiment, the detector line array 110 includes four light detectors 116, 118, 120, 122, with each of the light detectors 116, 118, 120, 122 being disposed at a different distance from the light sources 112, 114. For example, the light detectors 116, 118, 120, 122 can be disposed at 2 mm, 3 mm, 4 mm, and 6 mm, respectively, from each of the light sources 112, 114. Signals generated by the light detectors 116, 118, 120, 122 are supplied to the PPG control unit 94, which includes an analog to digital converter to generate PPG sensor digital data that can be processed by the one or more processors 82 to determine the arrival of the blood pressure pulse to the wrist-worn device. The PPG control unit 94 controls activation of the light sources 112, 114, and can alternately illuminate the light sources 112, 114 at a frequency sufficiently high to enable combined assessment of the PPG sensor digital data generated by illumination of the wrist with the different wavelengths provided by the light sources 112, 114.

The generated ICG/EKG digital data and the PPG sensor digital data can be transferred to, and stored in, the RAM 98 for any suitable subsequent use. For example, the data can be: 1) processed by the one or more processors 82 to determine PTTs and corresponding blood pressure values for the subject, 2) displayed on the display 86, and/or 3) output via the input/output devices 88 for any suitable purpose such as to a health care professional and/or a monitoring service. In many embodiments, the one or more processors 82 processes the ICG/EKG and PPG sensor digital data to generate trending data for a time period based on the one or more relative blood pressure values. Such trending data can be generated for any suitable time period, for example, for one or more days, one or more weeks, one or more months, and/or one or more years. One or more blood pressure values and/or associated trending data can be: 1) stored in the RAM 98, 2) displayed on the display 86, and/or 3) output via the input/output devices 88 for any suitable purpose such as to a health care professional and/or a monitoring service.

Figure 8:
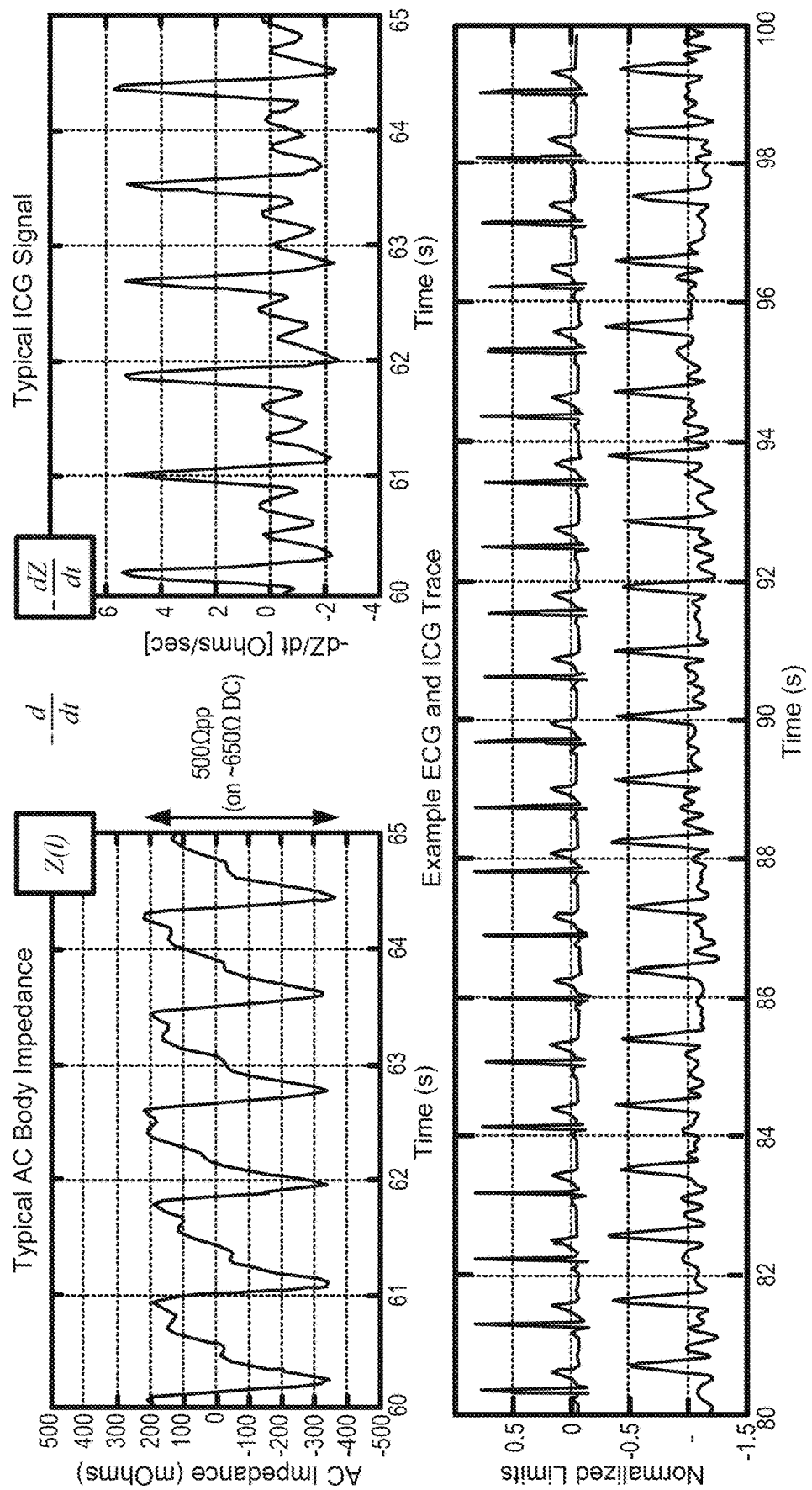
FIG. 8 shows typical EKG and ICG data traces, in accordance with many embodiments.

FIG. 8 shows typical EKG and ICG data traces, in accordance with many embodiments. AC body impedance Z(t) is calculated using the applied drive current/(t) and the measured resulting voltage difference signal V(t) per equation (6).

$$Z(t)=V(t)/I(t) \quad (6)$$

The ICG signal is then generated by calculating the negative time differential of Z(t) as shown in equation (7).

$$\text{ICG Signal}=-dZ/dt \quad (7)$$

The EKG signal is generated by voltages generated within the body having variations at a much lower frequency (e.g., 0.05-100 Hz) in comparison to the relatively higher frequency of the impedance drive current (e.g., 85 kHz). Accordingly, signals from the first and second sense electrodes 58, 62 can be processed to generate both the ICG and the EKG traces. When both the EKG and the ICG traces are generated, the pre-ejection period (PEP) can be determined. While the PEP time period does not correlate well with blood pressure, it may correlate with an extent of vasomotion (vasodilation and vasoconstriction) and thereby serve as an additional factor that can be used to correlate blood pressure with measured PTT. For example, a relationship can be developed where predicted blood pressure is a correlated function of both PTT and PEP.

Figure 9:
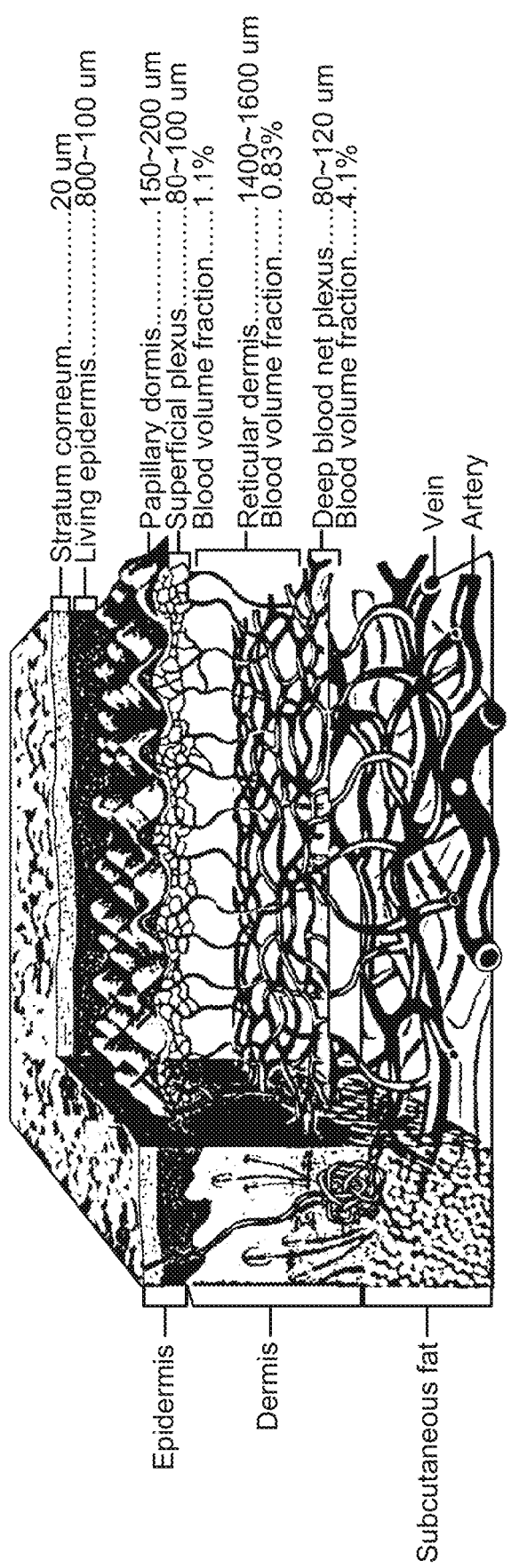
FIG. 9 illustrates subsurface layers of a subject.

FIG. 9 illustrates subsurface layers of a subject. The illustrated layers include: 1) the stratum corneum (about 20 µm thick), 2) the living epidermis (80 to 100 µm thick), 3) the papillary dermis (150 to 200 µm thick), 4) the superficial plexus (80 to 100 µm thick with a blood volume fraction of about 1.1%), 5) the reticular dermis (1400 to 1600 µm thick with a blood volume faction of about 0.83%), and 6) the deep blood net plexus (80 to 120 µm thick with a blood volume fraction of about 4.1%). Upon arrival to the wrist, the blood pressure pulse arrives at the deep blood net plexus layer before propagating to the overlying layers. As vasomotion (vasodilation and vasoconstriction) plays an important role in regulating blood flow in arterioles and capillaries further downstream in the arterial tree, using the PPG sensor to detect the arrival of the blood pressure pulse in the deep blood net plexus layer may increase the strength of the correlation between blood pressure and PTT by reducing vasomotion induced variability of PTT in shallower layers more subject to vasomotion induced variation in pulse wave velocity of the blood pressure pulse.

Figure 10:
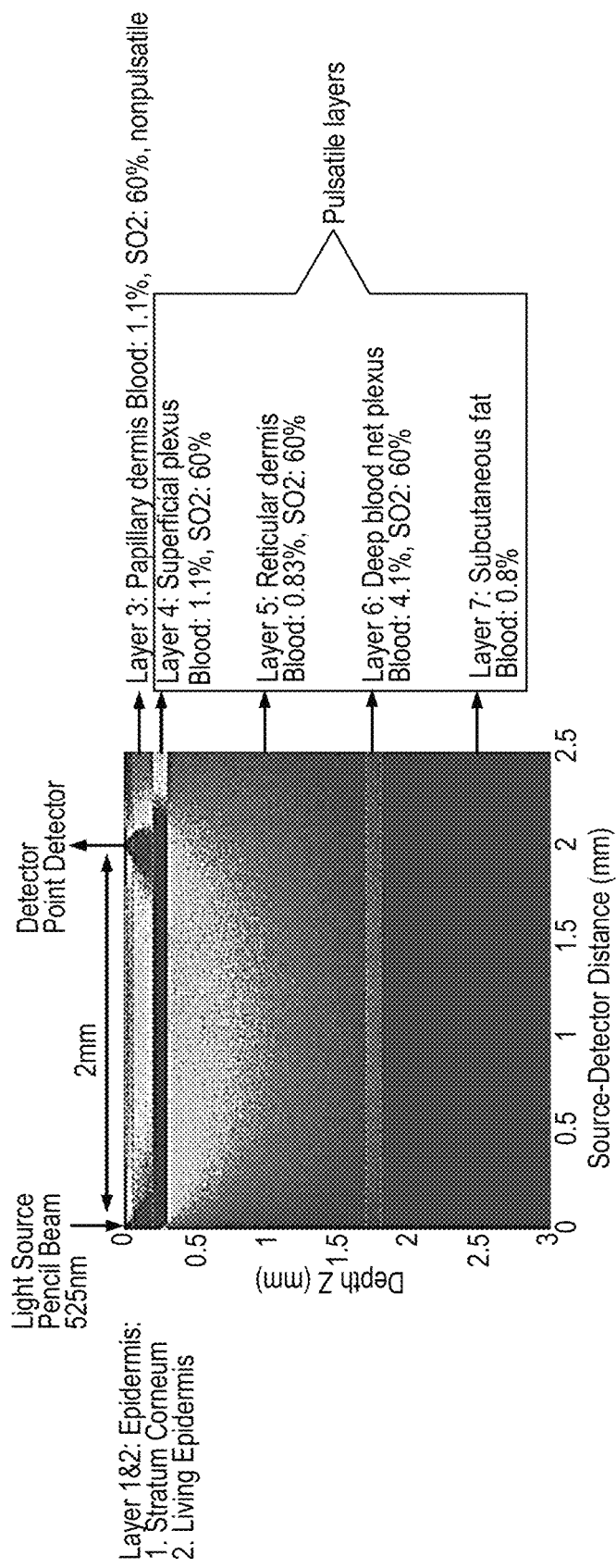
FIGS. 10 through 12 illustrate detection of different mean penetration depths of light emitted by a PPG sensor having returning light detectors disposed at different distances from each of two light sources of the PPG sensor, in accordance with many embodiments.
Figure 11:
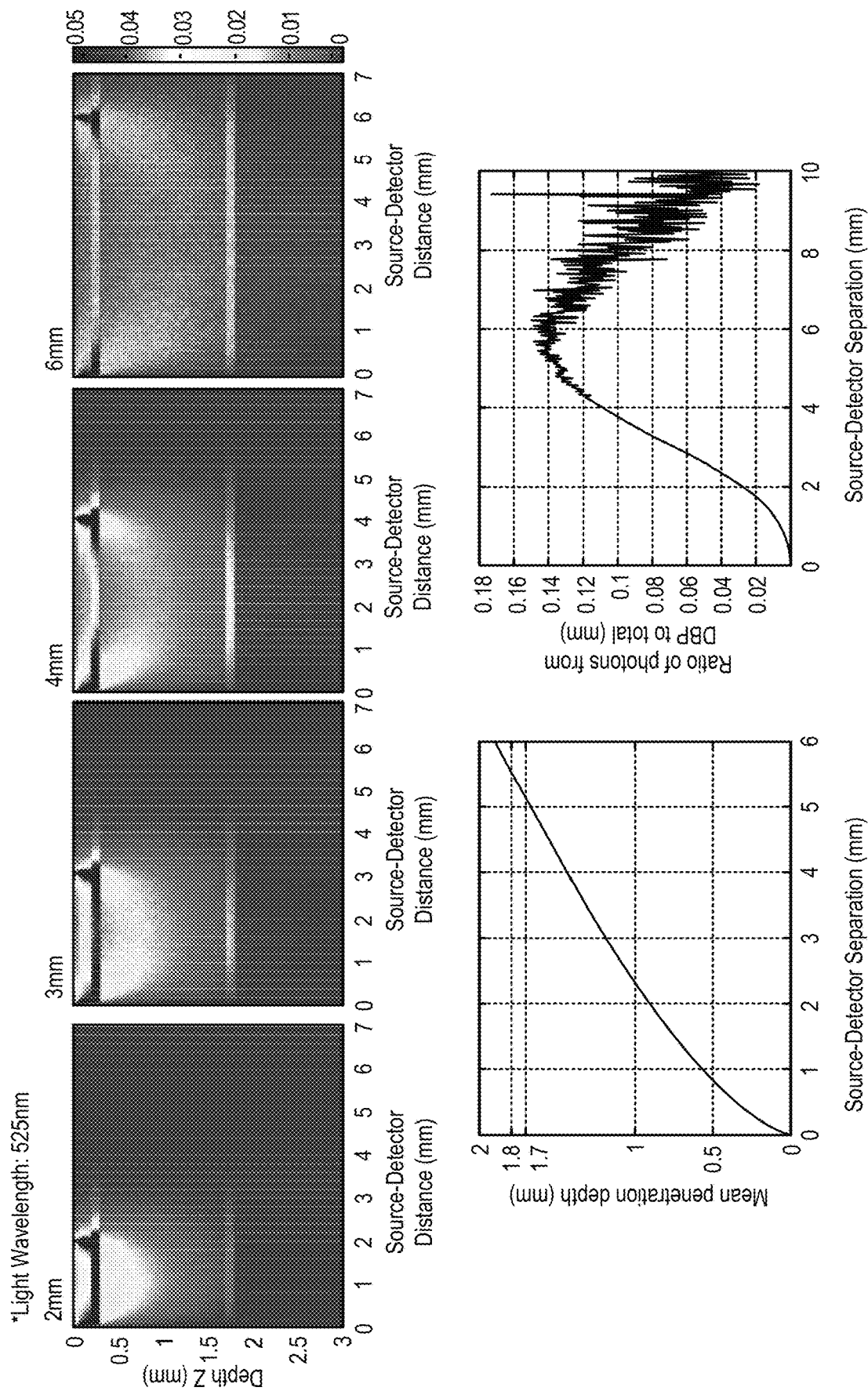
Figure 12:
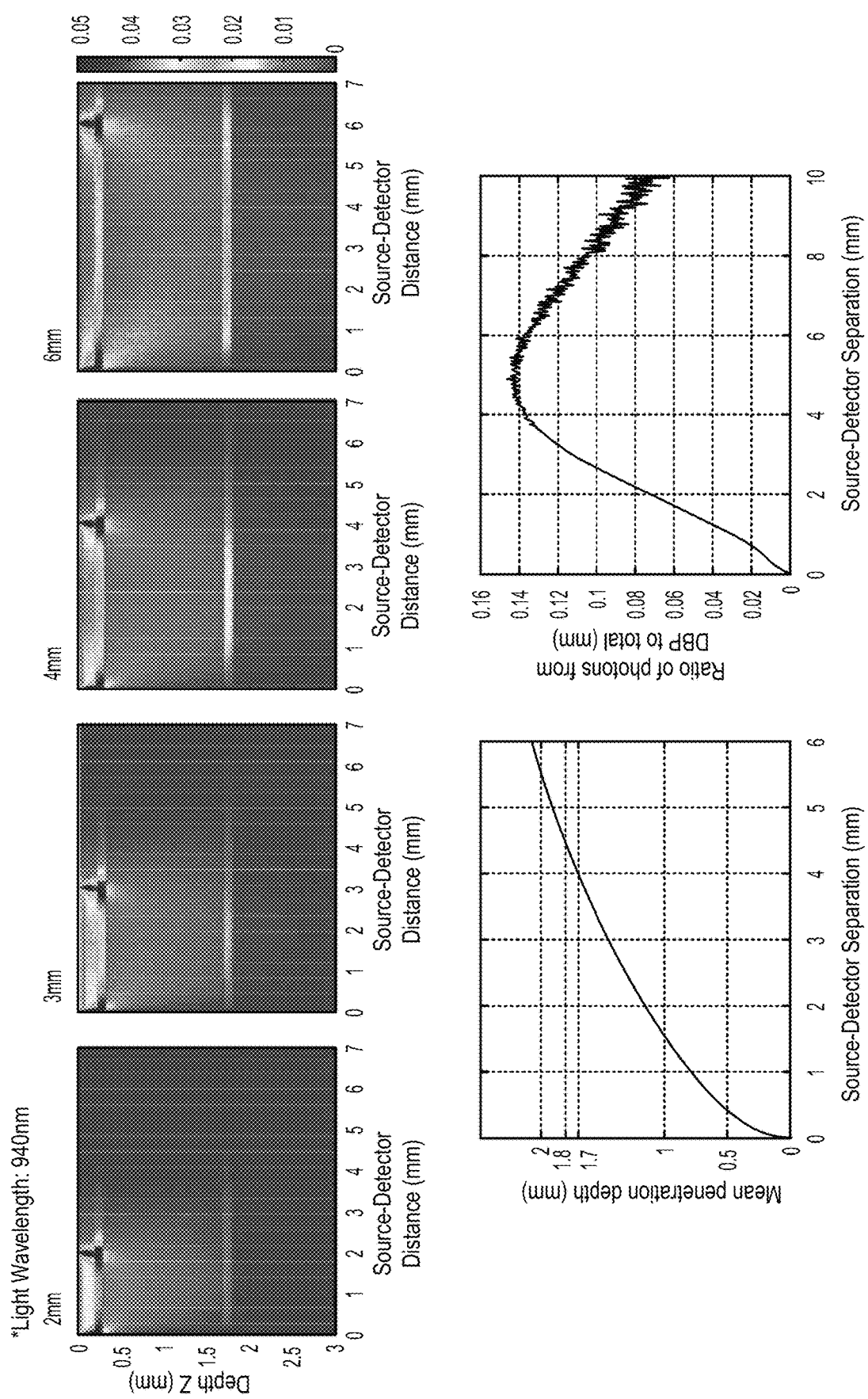
Figure 13:
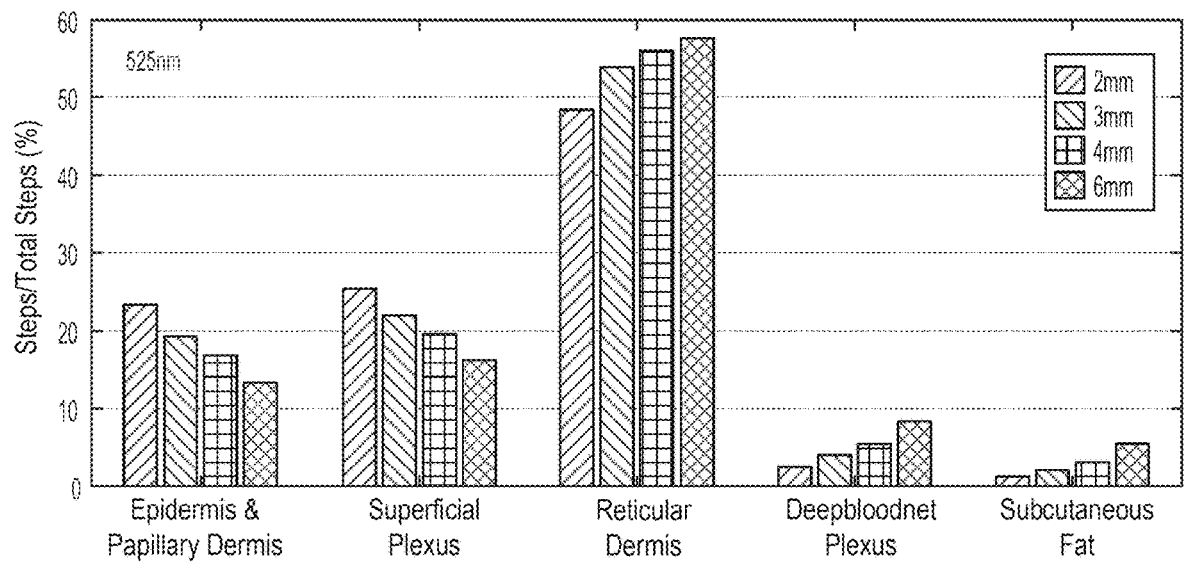
FIGS. 13 and 14 show relative contribution by subsurface layer to returning light detected by the light detectors disposed at different distances for two different light source wavelengths, in accordance with many embodiments.
Figure 14:
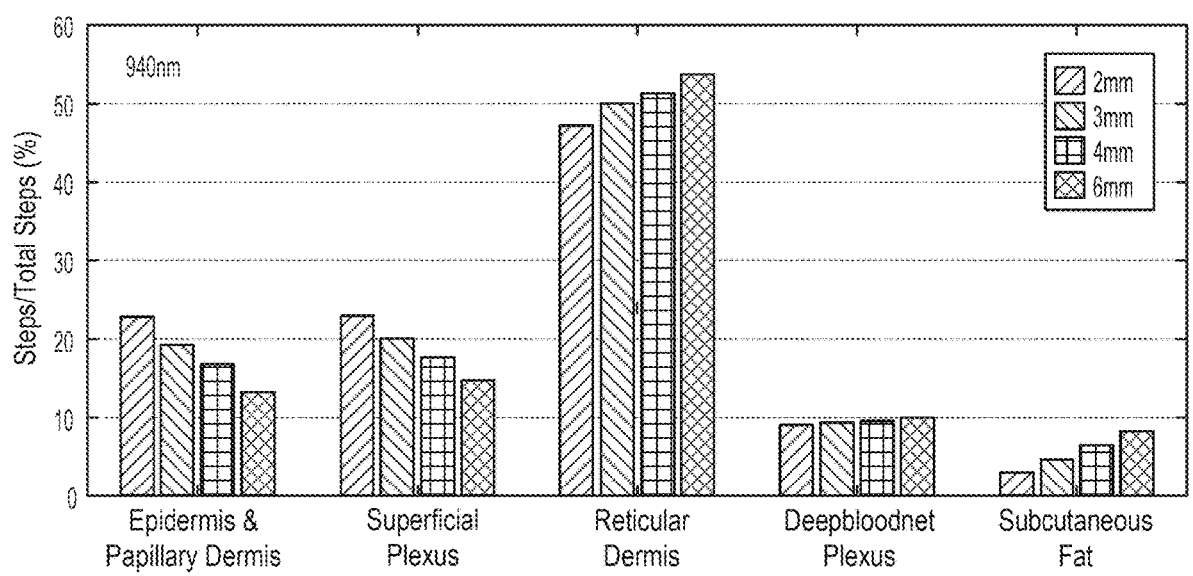
Figure 15:
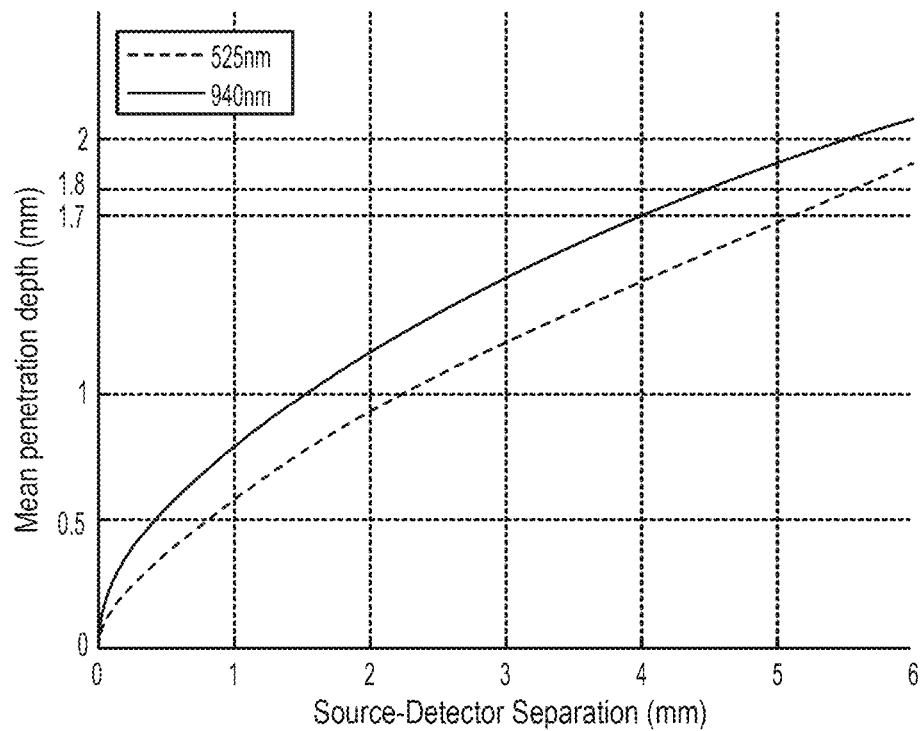
FIG. 15 illustrates variation of mean penetration depth as a function of source-detector separation for two different source light wavelengths, in accordance with many embodiments.
Figure 16:
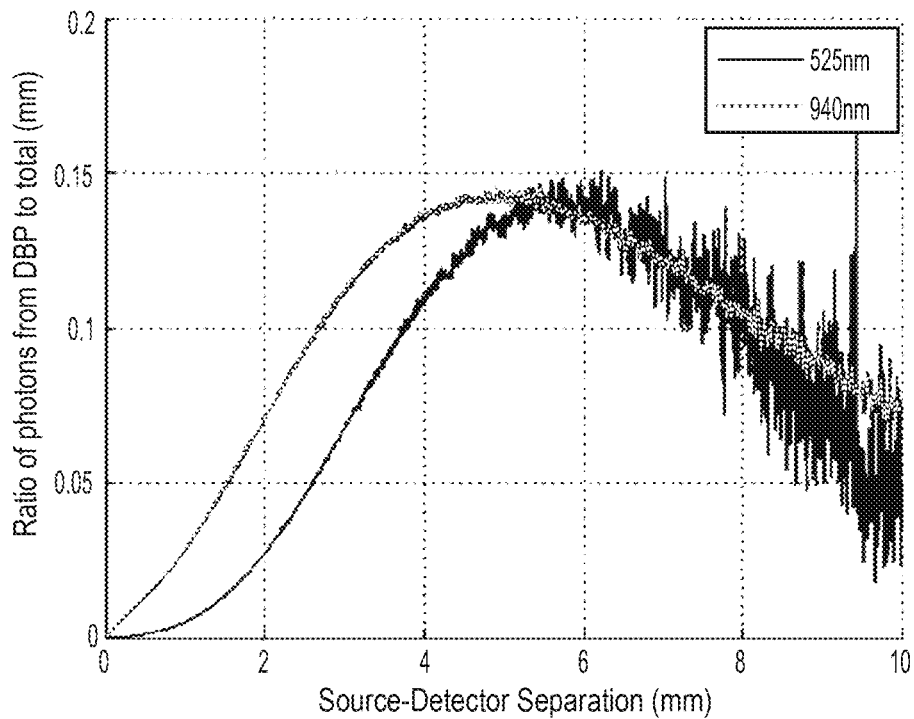
FIG. 16 illustrates variation of the ratio of photons from the deep blood plexus (DBP) layer as a function of source-detector separation for two different source light wavelengths, in accordance with many embodiments.

FIGS. 10 through 12 illustrate detection of different mean penetration depths of light emitted by a PPG sensor having returning light detectors disposed at different distances from each of two light sources of the PPG sensor, in accordance with many embodiments. FIG. 10 illustrates distribution of sensing depths for a combination of a 525 nm light source and a point detector disposed 2 mm from the 525 nm light source. FIG. 11 illustrates distributions of sensing depths for the combination of a 525 nm light source and point detectors disposed at 2 mm, 3 mm, 4 mm, and 6 mm from the 525 nm light source, as well as corresponding graphs of mean penetration depth and ratio of photons from the deep blood net plexus layer to the total detected returned light as a function of source-detector separation. FIG. 12 illustrates distributions of sensing depths for the combination of a 940 nm light source and point detectors disposed at 2 mm, 3 mm, 4 mm, and 6 mm from the 940 nm light source, as well as corresponding graphs of mean penetration depth and ratio of photons from the deep blood net plexus layer to the total detected returned light as a function of source-detector separation. FIGS. 13 and 14 show contribution of the total detected returned light for each layer for each wavelength and source-detector separation. FIGS. 15 and 16 show combined graphs corresponding to the graphs of FIGS. 11 and 12.

Using the data illustrated in FIGS. 10 through 16, the signals from the detectors 116, 118, 120, 122 generated for each of the light wavelengths generated by the light sources 112, 114 can be processed to detect arrival of the blood pressure pulse within a selected layer (e.g., with the deep blood net plexus layer). For example, arrival of the blood pressure pulse within the reticular dermis layer can be detected first due to the large percentage of the returning light incident on the detectors 116, 118, 120, 122 that returns from the reticular dermis layer. Once the arrival time to the reticular dermis layer is determined, the signals during a suitable time interval prior to the arrival time to the reticular dermis layer can be combined and/or processed to focus attention on detecting the earlier arrival of the blood pressure pulse to the deep blood plexus layer. Typically, infrared (e.g., 940 nm wavelength) light penetrates deeper into the skin compared to visible light such as green (e.g., 525 nm wavelength) or red (e.g., 660 nm wavelength). Hence, a PPG waveform recorded from infrared light corresponds to light reflected from deeper blood vessels, while a PPG waveform recorded from green light corresponds to light reflected from capillaries near the skin surface. Since the blood pulse arrives at deeper blood vessels earlier than capillaries near the skin surface, the blood pulse appears in the infrared PPG before the green PPG at the same location (e.g., on the wrist). A cross correlation of infrared and green PPG signals can be used to determine the relative delay between the arrival of the blood pulse at deeper blood vessels and the arrival of the blood pulse at capillaries near the skin surface.

The PPG signal can first be filtered in one of several ways, for example with a low-pass filter or with a regression filter. The pulse arrival can be detected as the peak of the amplitude of the PPG signal, or the "zero crossing point". Alternatively, the PPG signal can be differentiated with respect to time and the differentiated signal used to determine a pulse arrival time. This signal processing can be performed on single pulses, leading to PTTs for each heartbeat. Or, the processing can be performed on signals that are an average from more than one pulse. One multi-beat averaging method is to first transform the signals (ICG or ECG, and also PPG) into the frequency domain using a Fourier Transform. Then a cross-correlation between the two transformed signals will give a PTT value.

Figure 17:
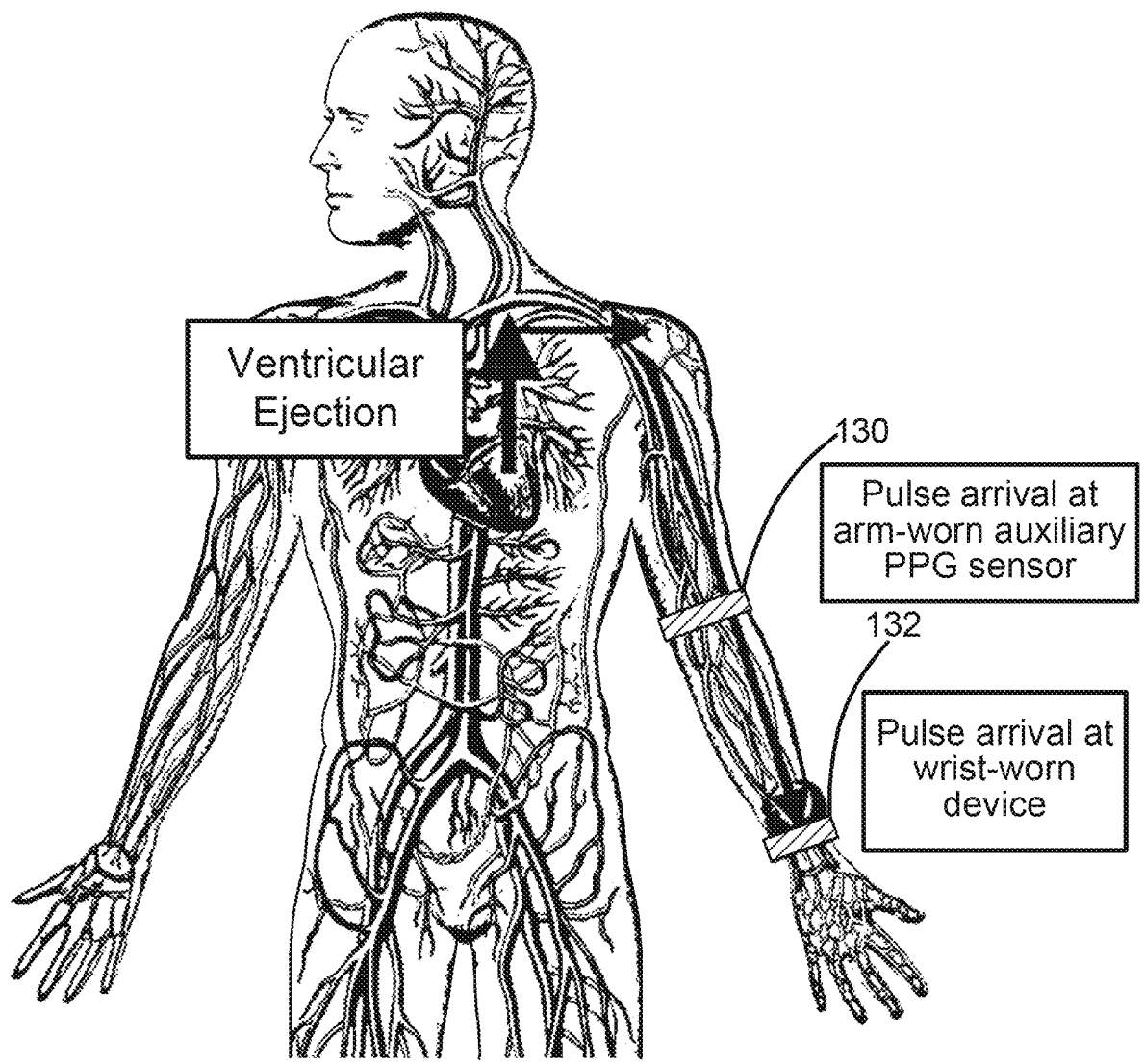
FIG. 17 illustrates a propagation path of a blood pressure pulse from ejection from the left ventricle past an auxiliary PPG sensor to a wrist on which a wrist-worn blood-pressure measurement device is worn, in accordance with many embodiments.

FIG. 17 illustrates another approach for measuring a PTT that can be used to generate one or more blood pressure values for a subject. The PTT measured in this approach is for the propagation of a blood pressure pulse from an arm-worn auxiliary device 130 to arrival at a wrist-worn device 132. The auxiliary device 130 and the wrist-worn device 132 can use any suitable approach for detecting the arrival of the blood-pressure pulse, such as via a PPG sensor as described herein.

Figure 18:
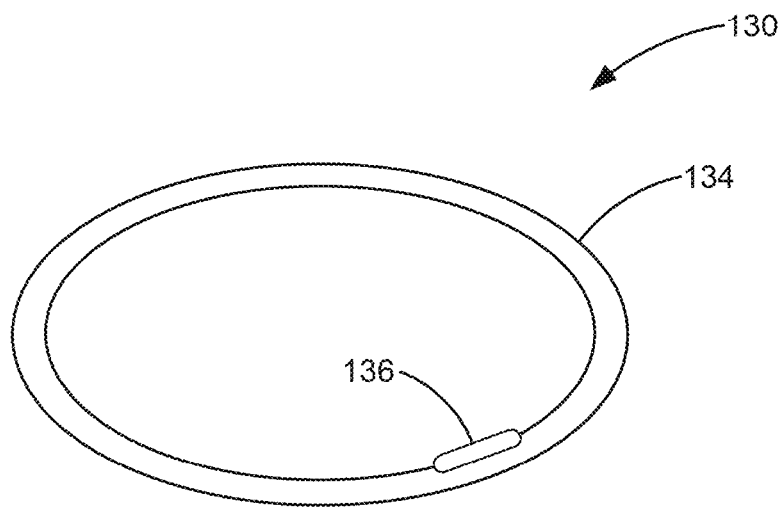
FIG. 18 is a schematic side view of an arm-worn auxiliary PPG sensor for a wrist-worn blood-pressure measurement device, in accordance with many embodiments.
Figure 19:
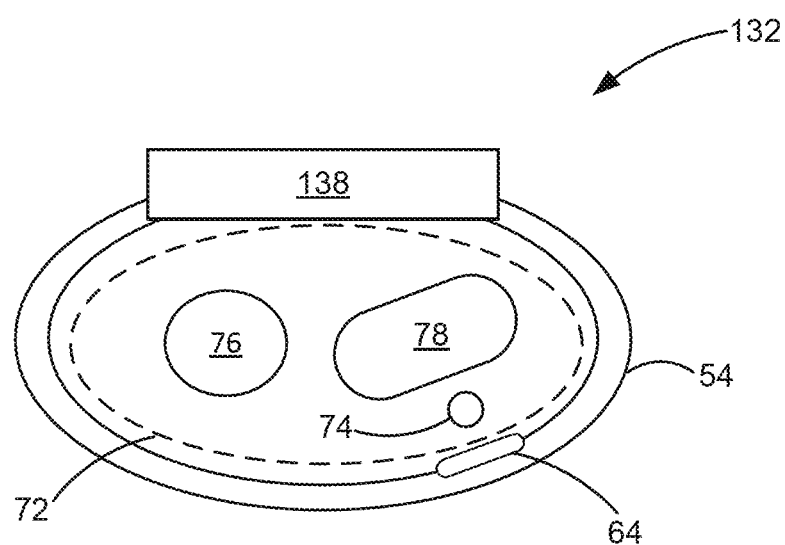
FIG. 19 is a cross-sectional view of another wrist-worn blood-pressure measurement device that can be used with the auxiliary PPG sensor of FIG. 18, in accordance with many embodiments.

FIGS. 18 and 19 show side views of the auxiliary device 130 and the wrist-worn device 132. The auxiliary device 130 includes an arm-worn elongate band 134 and an auxiliary PPG sensor 136 coupled to the band 134. The auxiliary device 130 can include one or more reference features or marks to as to enable reliable positioning and/or orientation of the auxiliary PPG sensor 136 relative to a selected underlying artery so as to detect arrival of the blood pressure pulse within the selected underlying artery. The wrist-worn device 132 can be configured similar to the wrist-worn devices 50, 70 with respect to the PPG sensor 64 and can have a main unit 138 that is configured similar to the main unit 52 with respect to all relevant functionality thereof.

It will be appreciated that personal information data may be utilized in a number of ways to provide benefits to a user of a device. For example, personal information such as health or biometric data may be utilized for convenient authentication and/or access to the device without the need of a user having to enter a password. Still further, collection of user health or biometric data (e.g., blood pressure measurements) may be used to provide feedback about the user's health and/or fitness levels. It will further be appreciated that entities responsible for collecting, analyzing, storing, transferring, disclosing, and/or otherwise utilizing personal information data are in compliance with established privacy and security policies and/or practices that meet or exceed industry and/or government standards, such as data encryption. For example, personal information data should be collected only after receiving user informed consent and for legitimate and reasonable uses of the entity and not shared or sold outside those legitimate and reasonable uses. Still further, such entities would take the necessary measures for safeguarding and securing access to collected personal information data and for ensuring that those with access to personal information data adhere to established privacy and security policies and/or practices. In addition, such entities may be audited by a third party to certify adherence to established privacy and security policies and/or practices. It is also contemplated that a user may selectively prevent or block the use of or access to personal information data. Hardware and/or software elements or features may be configured to block use or access. For instance, a user may select to remove, disable, or restrict access to certain health related applications that collect personal information, such as health or fitness data. Alternatively, a user may optionally bypass biometric authentication methods by providing other secure information such as passwords, personal identification numbers, touch gestures, or other authentication methods known to those skilled in the art.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method of determining one or more blood pressure values of a subject, the method comprising:
   propagating an alternating drive current through the subject between a first drive current electrode and a second drive current electrode, wherein the second drive current electrode is externally located on a wrist-worn device worn on a wrist of the subject and engaged with the subject so that a portion of the alternating drive current travels through a thorax of the subject, and wherein the first drive current electrode is non-invasively engaged with the subject's skin at the wrist;
   sensing voltage levels of the subject resulting from the alternating drive current via a first sense electrode and a second sense electrode, wherein the second sense electrode is externally located on the wrist-worn device and engaged with the subject so as to sense a voltage level induced by the alternating drive current, and wherein the first sense electrode is non-invasively engaged with the subject's skin at the wrist;
   processing the voltage levels to detect when a volume of blood is ejected from the left ventricle;
   processing output from a pulse arrival sensor coupled to the wrist-worn device to detect when a blood pressure pulse generated by ejection of the volume of blood from the left ventricle arrives at the wrist;
   calculating a pulse transit time (PTT) for transit of the blood pressure pulse from the left ventricle to the wrist; and
   determining one or more blood pressure values for the subject based on the PTT.

2. The method of claim 1, wherein:
   the second drive current electrode is in contact with a first finger of an arm of the subject opposite to an arm of the subject on which the wrist-worn device is worn when the alternating drive current is propagated and the voltage levels are sensed; and
   the second sense electrode is in contact with a second finger of the arm of the subject opposite to the arm of the subject on which the wrist-worn device is worn when the alternating drive current is propagated and the voltage levels are sensed.

3. The method of claim 2, wherein each of the first drive current electrode and the first sense electrode are located on the wrist-worn device so that contact pressure between the first finger and the second drive current electrode and contact pressure between the second finger and the second sense electrode increases contact pressure between the wrist and each of the first drive current electrode and the first sense electrode.

4. The method of claim 3, wherein:
   the wrist-worn device comprises an elongate wrist band; and
   the first drive current electrode, the second drive current electrode, the first sense electrode, and the second sense electrode are disposed on the elongate wrist band.

5. The method of claim 1, wherein each of the first drive current electrode, the second drive current electrode, the first sense electrode, and the second sense electrode is a dry electrode.

6. The method of claim 1, wherein the alternating drive current is propagated and the voltage levels are sensed when each of the second drive current electrode and the second sense electrode is contacted with skin on the subject's thorax.

7. The method of claim 1, wherein the pulse arrival sensor comprises a PPG sensor.

8. The method of claim 7, further comprising processing output from the PPG sensor to determine a tone of the subject's blood vessels, and wherein the one or more blood pressure values are further based on the tone of the subject's blood vessels.

9. The method of claim 7, further comprising detecting different mean penetration depths of light emitted by the PPG sensor by using at least two light detectors disposed at different distances from a light source of the PPG sensor to detect when the blood pressure pulse arrives at the wrist at a deeper of the different mean penetration depths.

10. The method of claim 9, further comprising processing one or more signals from the PPG sensor to detect when the blood pressure pulse arrives at the deep blood plexus (DBP) layer at the wrist.

11. The method of claim 7, further comprising detecting different mean penetration depths of light emitted by the PPG sensor by emitting different wavelengths of light from different light sources.

12. The method of claim 11, wherein the different light sources comprises at least two of an infra-red light source, a red light source, or a green light source.

13. The method of claim 11, wherein the different wavelengths of light comprise 525 nm and 940 nm.

14. The method of claim 9, comprising processing one or more signals from the PPG sensor to detect when the blood pressure pulse arrives at the wrist within the subject's radial artery.

15. The method of claim 1, wherein:
   the pulse arrival sensor comprises a pulse pressure sensor; and
   the pulse pressure sensor comprises at least one of a pressure transducer, an accelerometer, or a strain gauge.

16. The method of claim 1, further comprising calibrating the one or more blood pressure values based on calibration data comprising a reference blood pressure value for the subject and a reference PTT for transit of a reference blood pressure pulse from the left ventricle to the wrist.

17. The method of claim 1, further comprising calculating trending data for a time period based on the one or more blood pressure values.

18. The method of claim 17, wherein the time period comprises one or more days, one or more weeks, one or more months, or one or more years.

19. The method of claim 1, further comprising transmitting the one or more blood pressure values to a mobile device, table, tablet, computer, or database.

20. The method of claim 1, further compromising generating an electrocardiogram (EKG) for the subject from one or more signals generated by a set of the first drive current electrode, the second drive current electrode, the first sense electrode, and the second sense electrode.

\* \* \* \* \*